(12) United States Patent
Brookheart et al.

(10) Patent No.: US 11,534,423 B2
(45) Date of Patent: Dec. 27, 2022

(54) METHODS AND COMPOSITIONS FOR IMPROVING EXERCISE ENDURANCE, PERFORMANCE, OR TOLERANCE

(71) Applicants: Rita Brookheart, St. Louis, MO (US); Brian Finck, St. Louis, MO (US)

(72) Inventors: Rita Brookheart, St. Louis, MO (US); Brian Finck, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/732,740

(22) Filed: Jan. 2, 2020

(65) Prior Publication Data

US 2020/0215032 A1 Jul. 9, 2020

Related U.S. Application Data

(60) Provisional application No. 62/798,028, filed on Jan. 29, 2019, provisional application No. 62/787,895, filed on Jan. 3, 2019.

(51) Int. Cl.
*A61K 31/40* (2006.01)
*C12N 15/113* (2010.01)
*A61P 21/00* (2006.01)

(52) U.S. Cl.
CPC .............. *A61K 31/40* (2013.01); *A61P 21/00* (2018.01); *C12N 15/1137* (2013.01); *C12N 2310/11* (2013.01); *C12N 2310/122* (2013.01); *C12N 2310/14* (2013.01); *C12N 2320/30* (2013.01)

(58) Field of Classification Search
CPC ............... A61K 31/40; C12N 15/1137; C12N 2310/14; C12N 2310/122; C12N 2310/11; A61P 21/00
See application file for complete search history.

(56) References Cited

U.S. PATENT DOCUMENTS

2019/0125829 A1* 5/2019 Pajvani .............. A61K 38/1709

FOREIGN PATENT DOCUMENTS

WO WO-2018193075 A1 * 10/2018 ............. A61K 31/40

OTHER PUBLICATIONS

Hawkins et al (J. Pharm. Exp. Therap. 326(3): 801-808, 2008) (Year: 2008).*
Aswathi et al (Hereditary Genetics 2015, S7, 3 pages) (Year: 2015).*
Brown et al (Am J Physiol Regul Integr Comp Physiol 300: R605-R615, 2011) (Year: 2011).*
Rodriguez-Miguelez et al (J Physiol 595.5 (2017) pp. 1423-1425) (Year: 2017).*
Sawyer et al (BMC Sports Science, Medicine and Rehabilitation (2018) 10:19, 8 pages) (Year: 2018).*
Pastre et al (BMC Pulmonary Medicine 2014, 14:74, 8 pages) (Year: 2014).*
Solomon et al (Current Opinion in Pharmacology 2017, 34:132-139) (Year: 2017).*
Casaburi et al (Thorax 61(7): 551-552, 2006) (Year: 2006).*
Adzhubei, I. A., Schmidt, S., Peshkin, L., Ramensky, V. E., Gerasimova, A., Bork, P., . . . Sunyaev, S. R. (2010). A method and server for predicting damaging missense mutations. *Nature Methods*, 7(4), 248-249.
Aten, E., Brasz, L. C., Bornholdt, D., Hooijkaas, I. B., Porteous, M. E., Sybert, V. P., . . . den Dunnen, J. T. (2010). Keratosis Follicularis Spinulosa Decalvans is caused by mutations in MBTPS2. *Human Mutation*, 31(10), 1125-1133.
Bornholdt, D., Atkinson, T. P., Bouadjar, B., Catteau, B., Cox, H., De Silva, D., . . . Fuer Humangenetik, Z. (2013). Genotype-phenotype correlations emerging from the identification of missense mutations in MBTPS2. *Human Mutation*, 34, 587-594.
Brandl, K., Rutschmann, S., Li, X., Du, X., Xiao, N., Schnabl, B., . . . Beutler, B. (2009). Enhanced sensitivity to DSS colitis caused by a hypomorphic Mbtps1 mutation disrupting the ATF6-driven unfolded protein response. *Proceedings of the National Academy of Sciences*, 106(9), 3300-3305.
Brown, M. S., Faust, J. R., Goldstein, J. L., Kaneko, I., & Endo, A. (1978). Induction of 3-hydroxy-3-methylglutaryl coenzyme A reductase activity in human fibroblasts incubated with compactin (ML-236B), a competitive inhibitor of the reductase. *The Journal of Biological Chemistry*, 253(4), 1121-1128.
Cohen, J. C., Horton, J. D., & Hobbs, H. H. (2011). Human fatty liver disease: Old questions and new insights. *Science*, 332(6037), 1519-1523.
DeBose-Boyd, R. A., Brown, M. S., Li, W. P., Nohturfft, A., Goldstein, J. L., & Espenshade, P. J. (1999). Transport-dependent proteolysis of SREBP: Relocation of site-1 protease from Golgi to ER obviates the need for SREBP transport to Golgi. *Cell*, 99(7), 703-712.
Elagoz, A., Benjannet, S., Mammarbassi, A., Wickham, L., & Seidah, N. G. (2002). Biosynthesis and cellular trafficking of the convertase SKI-1/S1P: Ectodomain shedding requires SKI-1 activity. *The Journal of Biological Chemistry*, 277(13), 11265-11275.
Espenshade, P. J., Cheng, D., Goldstein, J. L., & Brown, M. S. (1999). Autocatalytic processing of site-1 protease removes propeptide and permits cleavage of sterol regulatory element-binding proteins. *Journal of Biological Chemistry*, 27(32), 22795-22804.
Espenshade, P. J., & Hughes, A. L. (2007). Regulation of sterol synthesis in eukaryotes. *Annual Review of Genetics*, 41, 401-427.
GeneCards Human Gene Database for MBTP1 Protein | MBTP1 Antibody downloaded from http://www.genecards.org/cgi-bin/carddisp.pl?gene=MBTPS11 on Oct. 19, 2017, 16 pages.
Goldstein, J. L., Hazzard, W. R., Schrott, H. G., Bierman, E. L., & Motulsky, A. G. (1973). Hyperlipidemia in coronary heart disease. I. Lipid levels in 500 survivors of myocardial infarction. *The Journal of Clinical Investigation*, 52(7), 1533-1543.
Gorski, JP, et al. Deletion of Mbtps1 (Pcsk8, S1p, Ski-1) Gene in steocytes Stimulates Soleus Muscle Regeneration and Increased Size and Contractile Force with Age. J. Biol. Chem. Feb. 26, 2016; 291(9):4308-22.

(Continued)

*Primary Examiner* — Richard A Schnizer

(57) ABSTRACT

Among the various aspects of the present disclosure is the provision of methods and compositions for improving exercise endurance, performance, or tolerance using an S1P inhibiting agent.

12 Claims, 18 Drawing Sheets

Specification includes a Sequence Listing.

(56) References Cited

OTHER PUBLICATIONS

Haghighi, A., Scott, C. A., Poon, D. S., Yaghoobi, R., Saleh-Gohari, N., Plagnol, V., & Kelsell, D. P. (2013). A missense mutation in the MBTPS2 gene underlies the X-linked form of Olmsted syndrome. *The Journal of Investigative Dermatology*, 133(2), 571-573.

Hawkins, J. L., Robbins, M. D., Warren, L. C., Xia, D., Petras, S. F., Valentine, J. J., . . . Harwood, H. J.( 2008). Pharmacologic inhibition of site 1 protease activity inhibits sterol regulatory element-binding protein processing and reduces lipogenic enzyme gene expression and lipid synthesis in cultured cells and experimental animals. *The Journal of Pharmacology and Experimental Therapeutics*, 326(3), 801-808.

Hay, B. A., Abrams, B., Zumbrunn, A. Y., Valentine, J. J., Warren, L. C., Petras, S. F., . . . Harwood, H. J. (2007). Aminopyrrolidineamide inhibitors of site-1 protease. *Bioorganic & Medicinal Chemistry Letters*, 17(16), 4411-4414.

Hong, J., Kim, K., Kim, J.-H., & Park, Y. (2017). The role of endoplasmic reticulum stress in cardiovascular disease and exercise. *International Journal of Vascular Medicine*, 2017, 9.

Hotamisligil, G. S. (2010). Endoplasmic reticulum stress and the inflammatory basis of metabolic disease. *Cell*, 140(6), 900-917.

Kim, J. Y., Garcia-Carbonell, R., Yamachika, S., Zhao, P., Dhar, D., Loomba, R., . . . Karin, M. (2018). ER stress drives lipogenesis and steatohepatitis via caspase-2 activation of S1P. *Cell*, 175(1), 133-145; e15.

Kim, J. B., Sarraf, P., Wright, M., Yao, K. M., Mueller, E., Solanes, G., . . . Spiegelman, B. M. (1998). Nutritional and insulin regulation of fatty acid synthetase and leptin gene expression through ADD1/SREBP1. *Journal of Clinical Investigation*, 101(1), 1-9.

Kondo, Y., Fu, J., Wang, H., Hoover, C., McDaniel, J. M., Steet, R., . . . Xia, L. (2018). Site-1 protease deficiency causes human skeletal dysplasia due to defective inter-organelle protein trafficking. *JCI Insight*, 3(14).

Kumar, P., Henikoff, S., & Ng, P. C. (2009). Predicting the effects of coding non-synonymous variants on protein function using the SIFT algorithm. Nature Protocols, 4(7), 1073-1081.

Lindert, U., Cabral, W. A., Ausavarat, S., Tongkobpetch, S., Ludin, K., Barnes, A. M., . . . Shotelersuk, V. (2016). MBTPS2 mutations cause defective regulated intramembrane proteolysis in X-linked osteogenesis imperfecta. *Nature Communications*, 7, 11920.

Marschner, K., Kollmann, K., Schweizer, M., Braulke, T., & Pohl, S. (2011). A key enzyme in the biogenesis of lysosomes is a protease that regulates cholesterol metabolism. Science (New York, N.Y.), 333(6038), 87-90.

Mathe, E., Olivier, M., Kato, S., Ishioka, C., Hainaut, P., & Tavtgian, S.V. (2006). Computational approaches for predicting the biological effect of p53 missense mutations: A comparison of three sequence analysis based methods. Nucleic Acids Research, 34(5), 1317-1325.

Miller, T., Al-Lozi, M. T., Lopate, G., & Pestronk, A. (2002). Myopathy with antibodies to the signal recognition particle: clinical and pathological features. *Journal of Neurology, Neurosurgery, and Psychiatry*, 73(4), 420-8.

Mozaffar, T., & Pestronk, A. (2000). Myopathy with anti-Jo-1 antibodies: pathology in perimysium and neighbouring muscle fibres. *Journal of Neurology, Neurosurgery, and Psychiatry*, 68(4), 472-8.

Naiki, M., Mizuno, S., Yamada, K., Yamada, Y., Kimura, R., Oshiro, M., . . . Wakamatsu, N. (2012). MBTPS2 mutation causes BRESEK/BRESHECK syndrome. *American Journal of Medical Genetics Part A*, 158A(1), 97-102.

Nakayama, J., Iwasaki, N., Shin, K., Sato, H., Kamo, M., Ohyama, M., . . . Arinami, T. (2011). A Japanese case of ichthyosis follicularis with atrichia and photophobia syndrome with an MBTPS2 mutation. *Journal of Human Genetics*, 56(3), 250-252.

Nohturfft, A., DeBose-Boyd, R. A., Scheek, S., Goldstein, J. L., & Brown, M. S. (1999). Sterols regulate cycling of SREBP cleavage-activating protein (SCAP) between endoplasmic reticulum and Golgi. *Proceedings of the National Academy of Sciences of the United States of America*, 96(20), 11235-11240.

Oeffner, F., Fischer, G., Happle, R., König, A., Betz, R. C., Bornholdt, D., . . . Grzeschik, K.-H. (2009). IFAP syndrome is caused by deficiency in MBTPS2, an intramembrane zinc metalloprotease essential for cholesterol homeostasis and ER stress response. *The American Journal of Human Genetics*, 84(4), 459-467.

Raggo, C., Rapin, N., Stirling, J., Gobeil, P., Smith-Windsor, E., O'Hare, P., & Misra, V. (2002). Luman, the cellular counterpart of herpes simplex virus VP16, is processed by regulated intramembrane proteolysis. *Molecular and Cellular Biology*, 22(16), 5639-5649.

Ramos da Palma, J., Cendron, L., Seidah, N. G., Pasquato, A., & Kunz, S. (2015). Mechanism of folding and activation of subtilisin kexin isozyme-1 (SKI-1)/site-1 protease (S1P). *Journal of Biological Chemistry*, 1(1), jbc.M115.677757.

Rawson, R. B., Cheng, D., Brown, M. S., & Goldstein, J. L. (1998). Isolation of cholesterol-requiring mutant Chinese hamster ovary cells with defects in cleavage of sterol regulatory element-binding proteins at site 1. *The Journal of Biological Chemistry*, 273(43), 28261-28269.

Rotterdam ESHRE/ASRM-Sponsored PCOS Consensus Workshop Group (2004). Revised 2003 consensus on diagnostic criteria and long-term health risks related to polycystic ovary syndrome. *Fertility and Sterility*, 81(1), 19-25.

Rutschmann, S., Crozat, K., Li, X., Du, X., Hanselman, J. C., Shigeoka, A. A., . . . Beutler, B. (2012). Hypopigmentation and maternal-zygotic embryonic lethality caused by a Hypomorphic Mbtps1 mutation in mice. G3; *Genes|genomes|genetics*, 2(4), 499-504.

Sakai, J., Rawson, R. B., Espenshade, P. J., Cheng, D., Seegmiller, A. C., Goldstein, J. L., & Brown, M. S. (1998). Molecular identification of the sterol-regulated luminal protease that cleaves SREBPs and controls lipid composition of animal cells. *Molecular Cell*, 2(4), 505-514.

Schwarz, J. M., Cooper, D. N., Schuelke, M., & Seelow, D. (2014). MutationTaster2: mutation prediction for the deep-sequencing age. *Nature Methods*, 11(4), 361-362.

Seidah, N. G., Mowla, S. J., Hamelin, J., Mamarbachi, A. M., Benjannet, S., Touré, B. B., . . . Marcinkiewicz, M. (1999). Mammalian subtilisin/kexin isozyme SKI-1: A widely expressed proprotein convertase with a unique cleavage specificity and cellular localization. *Proceedings of the National Academy of Sciences of the United States of America*, 96(4), 1321-1326.

Shen, J., Chen, X., Hendershot, L., & Prywes, R. (2002). ER stress regulation of ATF6 localization by dissociation of BiP/GRP78 binding 3(1), 99-111.

Shimomura, I., Shimano, H., Horton, J. D., Goldstein, J. L., & Brown, M. S. (1997). Differential expression of exons 1a and 1c in mRNAs for sterol regulatory element binding protein-1 in human and mouse organs and cultured cells. *The Journal of Clinical Investigation*, 99(5), 838-845.

Skinner, J. R., Shew, T. M., Schwartz, D. M., Tzekov, A., Lepus, C. M., Abumrad, N. A., & Wolins, N. E. (2009). Diacylglycerol enrichment of endoplasmic reticulum or lipid droplets recruits perilipin 3/TIP47 during lipid storage and mobilization. *Journal of Biological Chemistry*, 284(45), 30941-30948.

Stirling, J., & O'hare, P., (2006). CREB4, a transmembrane bZip transcription factor and potential new substrate for regulation and cleavage by S1P. *Molecular Biology of the Cell*, 17(1), 413-426.

Snapp, E. L., Iida, T., Frescas, D., Lippincott-Schwartz, J., & Lilly, M. A. (2004). The Fusome Mediates Intercellular Endoplasmic Reticulum Connectivity in *Drosophila* Ovarian Cysts. *Molecular Biology of the Cell*, 15(10), 4512-4521.

Tavtigian, S. V., Deffenbaugh, A. M., Yin, L., Judkins, T., Scholl, T., Samollow, P. B., . . . Thomas, A. (2006). Comprehensive statistical study of 452 BRCA1 missense substitutions with classification of eight recurrent substitutions as neutral. *Journal of Medical Genetics*, 43(4), 295-305.

Uchida, L., Urata, S., Ulanday, G. E. L., Takamatsu, Y., Yasuda, J., Morita, K., & Hayasaka, D. (2016). Suppressive effects of the Site 1 Protease (S1P) inhibitor, PF-429242, on Dengue virus propagation. *Viruses*, 8(2), 46.

(56) References Cited

OTHER PUBLICATIONS

Yang, J., Goldstein, J. L., Hammer, R. E., Moon, Y. A., Brown, M. S., & Horton, J. D. (2001). Decreased lipid synthesis in livers of mice with disrupted Site-1 protease gene. *Proceedings of the National Academy of Sciences of the United States of America*, 98(24), 13607-13612.

Ye, J., Rawson, R. B., Komuro, R., Chen, X., Davé, U. P., Prywes, R., . . . Goldstein, J. L. (2000). ER stress induces cleavage of membrane-bound ATF6 by the same proteases that process SREBPs. *Molecular Cell*, 6(6), 1355-1364.

Zhang, J., Wang, Y., Cheng, R., Ni, C., Liang, J., Li, M., & Yao, Z. (2016). Novel MBTPS2 missense mutation causes a keratosis follicularis spinulosa decalvans phenotype: mutation update and review of the literature. Clinical and Experimental Dermatology, 41(7), 757-760.

\* cited by examiner

```
H. sapiens        RYNQEVGQTIPVFAFLGAMVV
P. troglodytes    RYNQEVGQTIPVFAFLGAMVV
M. musculus       RYNQEVGQTIPVFAFLGAMVA
R. norvegicus     RYNQEVGQTIPVFAFLGAMVA
C. griseus        RYNQEVGQTIPVFAFLGAMVA
B. taurus         RYNQEVGQTIPVFAFLGAMVV
C. lupus          RYNQEVGQTIPVFAFLGAMVV
D. rerio          RYNQEVGQTIPMFAFLGAMVV
X. tropicalis     RYNQDVGQTIPVFAFLGAMVV
```

METHODS AND COMPOSITIONS FOR IMPROVING EXERCISE ENDURANCE, PERFORMANCE, OR TOLERANCE

CROSS-REFERENCE TO RELATED APPLICATIONS

This, application claims priority from U.S. Provisional Application Ser. No. 62/787,895 filed on 3 Jan. 2019 and from U.S. Provisional Application Ser. No. 62/798,028 filed on 29 Jan. 2019, which are incorporated herein by reference in their entireties.

STATEMENT REGARDING FEDERALLY SPONSORED RESEARCH OR DEVELOPMENT

This invention was made with government support under HL145325 and DK056341 awarded by National Institutes of Health. The government has certain rights in the invention.

MATERIAL INCORPORATED-BY-REFERENCE

Not applicable.

FIELD OF THE INVENTION

The present disclosure generally relates to improving exercise tolerance or endurance.

SUMMARY OF THE INVENTION

Among the various aspects of the present disclosure is the provision of methods and compositions for improving exercise endurance or tolerance.

An aspect of the present disclosure provides for a method of treating a disease, disorder, or condition associated with reduced exercise tolerance or endurance in a subject. Another aspect of the present disclosure provides for a method of improving exercise tolerance or enhancing performance in a subject.

Another aspect of the present disclosure provides for a method of improving exercise tolerance or enhancing exercise performance in a subject comprising administering a therapeutically effective amount of a pharmaceutical composition comprising a S1P inhibiting agent. Another aspect of the present disclosure provides for a method of treating a disease, disorder, or condition associated with reduced exercise tolerance or endurance in a subject comprising administering a therapeutically effective amount of a pharmaceutical composition comprising a S1P inhibiting agent.

In some embodiments, the therapeutically effective amount of the pharmaceutical composition comprising a S1P inhibiting agent results in reduced or depleted S1P levels or reduced or depleted S1P activity.

In some embodiments, the therapeutically effective amount of the pharmaceutical composition comprising a S1P inhibiting agent further results in: improved exercise tolerance or improved exercise endurance in the subject; increased expression of genes encoding enzymes involved in fatty acid metabolism; higher capacity for fatty acid oxidation; enhanced fatty acid utilization; improved obesity-associated cardiometabolic outcomes; improved left ventricular (LV) function; enhanced mitochondrial metabolism; reduced respiratory exchange ratio (RER) value; increased long-chain fatty acid (LCFA) muscle uptake; elevated markers of fatty acid oxidation; or decreased serum triglyceride (TAG) levels; optionally, in response to exercise stimulus.

In some embodiments, the subject has reduced exercise tolerance or reduced exercise endurance.

In some embodiments, the subject has increased expression of S1P compared to a healthy subject; elevated serum cholesterol levels; elevated serum lipid levels; elevated levels of creatine kinase (CK); elevated aspartate aminotransferase; or enlarged mitochondria.

In some embodiments, the subject has a gain of function mutation or a missense mutation in a S1P transmembrane domain.

In some embodiments, the gain of function mutation or the missense mutation is a Pro1003Ser mutation corresponding to SEQ ID NO: 20, in the S1P transmembrane domain, wherein the S1P transmembrane domain of the S1P comprises SEQ ID NO: 19.

In some embodiments, the subject has or is suspected of having, or the disease disorder, or condition associated with exercise tolerance can be, obesity, type 2 diabetes (T2DM), heart failure (HF), mitochondrial disorders or diseases, cardiovascular disease (CVD), insulin resistance, hypertension, hyperCKemia, myoedema, rhabdomyolysis, idiopathic chronic muscle fatigue, reduced skeletal muscle function, disrupted skeletal muscle function or metabolism, cardiac abnormalities, or dysfunctional muscle, heart, or skeletal metabolism.

In some embodiments, the subject has muscle fatigue, swelling, or myoedema during or after physical activity.

In some embodiments, the subject is a mammal.

In some embodiments, the subject is a human, horse, or dog.

In some embodiments, the subject is an athlete or a subject in need of improving athletic performance.

In some embodiments, the S1P inhibiting agent is selected from a small molecule inhibitor of S1P.

In some embodiments, the S1P inhibiting agent is a genetic inhibition selected from an shRNA, an siRNA, and an anti-sense oligonucleotide (ASO).

In some embodiments, the genetic inhibition knocks out, knocks down, reduces, eliminates, or inhibits or reduces expression or activity of S1P.

In some embodiments, the S1P inhibiting agent is PF-429242:

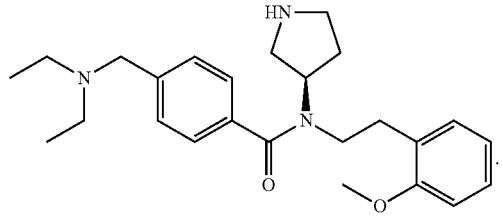

4-[(Diethylamino)methyl]-N-[2-(2-methoxyphenyl)ethyl]-N-(3R)-3-pyrrolidinyl-benzamide Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 2A shows a haemotoxylin and eosin (H&E) stained gastrocnemius of wild-type (WT) mice, and FIG. 2B shows an H&E stained gastrocnemius of SM-S1P$^{KO}$ mice. Representative images. n=3.

FIG. 3A shows that skeletal muscle from SM-S1P$^{KO}$ mice has reduced S1P mRNA. FIG. 3B shows that plasma triglyceride (TAG) levels are normal in sedentary SM-S1P$^{KO}$ mice. FIG. 3C shows that plasma cholesterol levels are normal in sedentary SM-S1P$^{KO}$ mice. n=4, *p<0.05.

FIG. 4A shows the total distance run during graded exercise test to exhaustion. FIG. 4B shows blood lactate levels taken immediately after exercise. FIG. 4C shows plasma TAG levels taken immediately after exercise. n=8, *p<0.05. For FIG. 4A-FIG. 4C, mice fasted 4 h prior to exercise.

FIG. 8A is a schematic of S1P protein with the Pro1003Ser mutation and S1P protein domains indicated, TM, transmembrane domain. FIG. 8B is a multispecies alignment of S1P amino acid sequences demonstrating the mutated proline 1003 residue is conserved (shown in bold). FIG. 8C shows mRNA expression levels of the MBTPS1 transcript in cultured control- and patient-derived skin fibroblasts. n=3. FIG. 8D shows Sanger sequencing trace files of patient genomic DNA (top) and cDNA (bottom)-derived PCR products at the MBTPS1 c.3007C>T locus. Intron-exon boundary (genomic) and exon-exon junction (cDNA) are indicated. Arrows denote the variant location. FIG. 8E is a Western blot of whole-cell lysates (60 µg) from SRD-12B cells transiently transfected with mock, WT S1P, or S1P Pro1003Ser plasmids after 24 hr. S1P-A, B, and C forms are indicated. Blots were probed with S1P and α-tubulin (loading control) antibodies. n=3. FIG. 8F shows SRD-12B cells were transfected as in FIG. 8E and grown either in medium supplemented with lipids and cholesterol (left column) or in lipid- and cholesterol-free medium (right column) for 7 days followed by fixation in methanol and crystal violet staining, as reported previously. Images are representative of three independent experiments.

FIG. 9A shows Sudan black staining of neutral lipids. FIG. 9B shows period acid-Schiff (PAS) staining for glycogen content.

FIG. 10C shows SRD-12B cells transiently transfected with FAS-Luc, Renilla, and WT S1P or S1P Pro1003Ser plasmids as indicated, after 10 hr, cells were treated with DMEM/F12 for 16 hr. Luciferase activities were measured and the ratio between firefly and Renilla luciferase activities was determined. FIG. 10D shows immunofluorescence of S1P, ER marker KDEL, and Golgi marker GM130 in S1P Pro1003Ser patient and control fibroblasts. Cells were transfected with FLAG-tagged WT S1P or S1P Pro1003Ser as indicated. Representative images are shown. All data are expressed as mean S.E. of three to five independent experiments, * indicates p value<0.05

FIG. 11A: H&E, FIG. 11B: ATPase, FIG. 11C: Sudan black, FIG. 11D: cytochrome oxidase images are at 200× magnification. FIG. 11E shows that occcasional muscle fibers show subsarcolemmal collections of mitochondria with lipid containing vacuoles (arrows) (Magnification 10000×), FIG. 11 F shows that some collections showed unusual mitochondrial collections, shapes, changes in cristae and increased glycogen particles (Magnification 30000×).

DETAILED DESCRIPTION OF THE INVENTION

Figure 1:
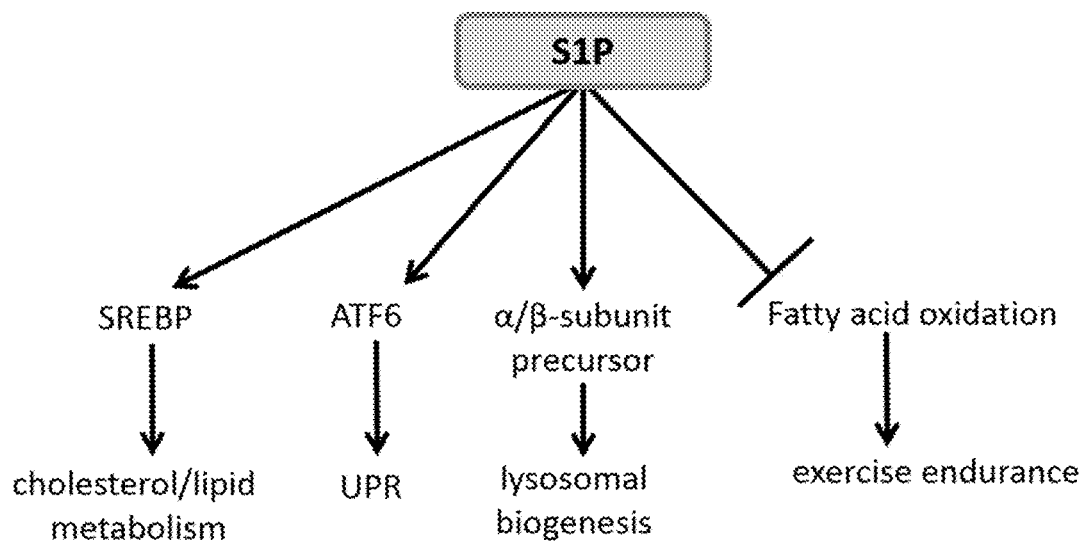
FIG. 1 is a schematic showing site-1 protease (S1P) regulation of key cellular functions. As described herein, it is believed skeletal muscle S1P inhibits fatty acid oxidation and decreases exercise endurance. S1P also regulates sterol regulatory element-binding protein (SREBP), activating transcription factor 6 (ATF6), and the unfolded protein response (UPR).

The present disclosure is based, at least in part, on the discovery that deactivation of Site-1 Protease (S1P) in skeletal muscle increases exercise endurance without the need for training. To date, a role for S1P in exercise capacity has not been reported, nor has the function of S1P chemical inhibitors (i.e., PF-429242) on muscle and exercise (e.g., athletic) performance been shown. As shown herein, the present disclosure provides for studies of exercise tolerance on muscle-specific Site-1 Protease knockout mice and control mice and gene expression in post-exercise Site-1 Protease knockout mice and control mice.

As described herein, inhibition of S1P in vivo improves exercise tolerance and endurance in mammals (e.g., humans, dogs, and horses), without the need for training. Combination of S1P inhibition with exercise training may exacerbate the exercise tolerance benefit observed in S1P inhibition-only mammals.

As described herein, S1P chemical inhibitors (e.g., PF-429242) can be used to enhance exercise or athletic performance in mammals. To date, use of these inhibitors for such purposes has not been reported.

As described herein, the studies also suggest a role for targeting S1P in the treatment of rhabdomyolysis.

As described herein, site-1 protease (S1P) deficiency can enhance acute exercise endurance and skeletal muscle function. The examples herein show the muscle of SM-S1P$^{KO}$ mice has a higher capacity for fatty acid oxidation, which could also be linked to their enhanced acute exercise performance.

Site-1 Protase (S1P)

Site-1 Protease (S1P), a Golgi-resident transmembrane domain protease, coordinates the adaptive response to physiologic or pathogenic stimuli by proteolytic activation of transcription factors important for maintaining cellular homeostasis. As described in Example 2, a patient was recently identified with a gain-of-function mutation in S1P, who exhibited marked muscle fatigue and idiopathic rhabdomyolysis following moderate physical activity. To examine the role of S1P in skeletal muscle and exercise S1P skeletal muscle-specific knockout mice (SM-S1P$^{KO}$ mice) were generated by crossing S1P floxed mice with mice expressing Cre recombinase driven by the human alpha-skeletal actin promoter. Example 2 describes data suggesting that the muscle of SM-S1P$^{KO}$ mice has a higher capacity for fatty acid oxidation, which could also be linked to their enhanced acute exercise performance.

Improving Exercise Tolerance or Endurance

The methods and compositions as described herein can improve exercise tolerance or improve exercise endurance in subjects. For example, the subject can be a subject with reduced exercise tolerance or reduced endurance or an athlete.

For example, the methods and compositions as described herein can improve exercise tolerance or improve exercise endurance in subjects with reduced exercise tolerance. For example, subjects with reduced exercise tolerance can be subjects with obesity, type 2 diabetes (T2DM), heart failure (HF), mitochondrial disorders or diseases, cardiovascular disease (CVD), or sarcopenia.

S1P Inhibiting Agent

As described herein, inhibitors of S1P can be used to improve exercise endurance or tolerance in a subject. For example, the S1P inhibiting agent can be used to improve exercise endurance or tolerance in subjects with a disease, disorder, or condition associated with reduced exercise tolerance or endurance.

It is well known that pharmacological and genetic inhibition can result in similar phenotypes and therapeutic effects. As such, pharmacological inhibition of S1P is expected to result in enhanced exercise tolerance as well.

It is well within the skill in the art to perform experiments using a lead synthetic ligand (e.g., S1P inhibiting agent) and confirm that the ligand is binding to the target and to determine off-target effects/protein interactions of ligand binding.

As an example, a S1P inhibiting agent can inhibit S1P, modulate mitochondrial function in skeletal muscle, increase exercise endurance, performance, or tolerance, increase expression of genes encoding enzymes involved in fatty acid metabolism (e.g., elevated markers of fatty acid oxidation), or decreased serum TAG levels, even without training.

For example, a S1P inhibiting agent can be PF-429242:

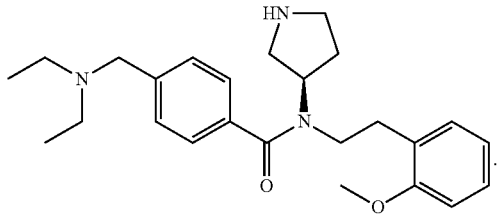

4-[(Diethylamino)methyl]-N-[2-(2-methoxyphenyl)ethyl]-N-(3R)-3-pyrrolidinyl-benzamide As another example, a S1P inhibiting agent can be Fatostatin:

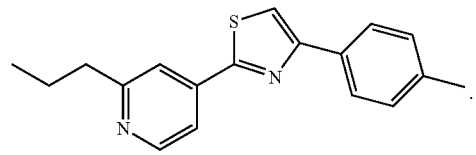

2-Propyl-4-(4-(p-tolyl)thiazol-2-yl)pyridine

As another example, a S1P inhibiting agent can be Betulin:

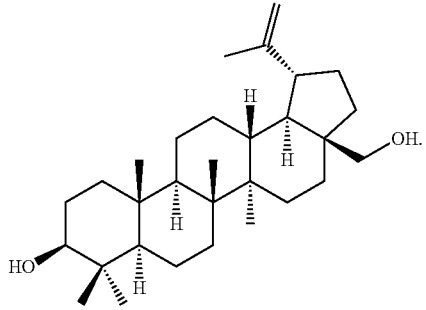

S1P Reduction, Elimination, or Inhibition by Small Molecule Inhibitors, shRNA, siRNA, or ASOs As described herein, a S1P inhibiting agent can be used for use to improve exercise endurance or tolerance. A S1P inhibiting agent can be used to reduce/eliminate S1P signals. For example, a S1P inhibiting agent can be a small molecule inhibitor of S1P. As another example, a S1P inhibiting agent can be a genetic inhibitor. As another example, a S1P inhibiting agent can be a short hairpin RNA (shRNA). As another example, a S1P inhibiting agent can be a short interfering RNA (siRNA).

As another example, S1P RNA can be targeted with antisense oligonucleotides (ASOs) as a therapeutic. Processes for making ASOs targeted to RNAs are well known; see e.g., Zhou et al. 2016 Methods Mol Biol. 1402:199-213. Except as otherwise noted herein, therefore, the process of the present disclosure can be carried out in accordance with such processes.

Disease, Disorder, or Condition Associated with Reduced Exercise Tolerance or Endurance Compositions and methods as described herein can be used to treat subjects with a disease, disorder, or condition associated with reduced exercise tolerance or endurance or a subject in need of increasing exercise tolerance.

For example, a disease, disorder, or condition associated with reduced exercise tolerance or endurance can be rhabdomyolysis or idiopathic chronic muscle fatigue.

As another example, the disease, disorder, or condition associated with reduced exercise tolerance or endurance can be obesity, reduced exercise capacity, reduced skeletal muscle function, disrupted skeletal muscle function or metabolism, or cardiac abnormalities (see e.g., Example 2). As another example, the disease, disorder, or condition associated with reduced exercise tolerance or endurance can be type 2 diabetes, heart failure (HF), mitochondrial disorders or diseases, cardiovascular disease (CVD), or sarcopenia.

The disease, disorder, or condition associated with reduced exercise tolerance or endurance can be associated with elevated plasma creatine kinase and aspartate aminotransferase levels following physical activity or enlarged mitochondria.

The disease, disorder, or condition associated with reduced exercise tolerance or endurance can be dysfunctional muscle metabolism.

The disease, disorder, or condition associated with reduced exercise tolerance or endurance can be associated with disruptions in heart and skeletal muscle function and metabolism.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine), Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$[Na$^+$])+0.41(fraction G/C content)−0.63(% formamide)−(600/l). Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Conservative Substitutions I

| Side Chain Characteristic | Amino Acid |
| --- | --- |
| Aliphatic Non-polar | G A P I L V |
| Polar-uncharged | C S T M N Q |
| Polar-charged | D E K R |
| Aromatic | H F W Y |
| Other | N Q D E |

Conservative Substitutions II

| Side Chain Characteristic | Amino Acid |
| --- | --- |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Conservative Substitutions III

| Original Residue | Exemplary Substitution |
| --- | --- |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met(M) | Leu, Phe, Ile |
| Phe (F) | Leu, Val, Ile, Ala |
| Pro (P) | Gly |
| Ser (S) | Thr |
| Thr (T) | Ser |
| Trp(W) | Tyr, Phe |
| Tyr (Y) | Trp, Phe, Tur, Ser |
| Val (V) | Ile, Leu, Met, Phe, Ala |

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, Tex.; Sigma Aldrich, Mo.; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Genome Editing

As described herein, S1P signals can be modulated (e.g., silenced, reduced, eliminated) using genome editing. Processes for genome editing are well known; see e.g. Aldi 2018 Nature Communications 9 (1911). Except as otherwise noted herein, therefore, the process of the present disclosure can be carried out in accordance with such processes. As an example, methods can include shRNA, siRNA, or ASOs for reduction, elimination of S1P. As another example, genome editing can comprise CRISPR/Cas9, CRISPR-Cpf1, TALEN, or ZNFs. Adequate blockage of S1P by genome editing can result in enhancement of exercise tolerance.

As an example, clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a $(N)_{20}$NGG target DNA sequence). This results in a double-strand break three nucleotides upstream of the NGG motif. The double strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, genomic editing, for example, using CRISPR/Cas systems could be useful tools for therapeutic applications for enhancing exercise tolerance to target cells by the removal of S1P signals.

For example, the methods as described herein can comprise a method for altering a target polynucleotide sequence in a cell comprising contacting the polynucleotide sequence with a clustered regularly interspaced short palindromic repeats-associated (Cas) protein.

As another example, genome editing can correct a deleterious mutation in the S1P gene, such as a missense mutation in exon 23 of the MBTPS1(NM_003791.3 c.3007C>T) gene that corresponded to a single amino acid substitution in the transmembrane domain of S1P (NP_003782.1 p.Pro1003Ser).As another example, the genome editing can knock out, knock down, or be any mutation that prohibits normal function of the S1P gene or results in a S1P deficiency or depletion.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Weals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of increasing exercise endurance, performance, or tolerance or treating a disease or condition associated with reduced exercise tolerance or endurance in a subject in need administration of a therapeutically effective amount of an S1P inhibiting agent, so as to improve exercise tolerance, performance, or endurance.

Methods described herein are generally performed on a subject in need thereof. A subject in need of the therapeutic methods described herein can be a subject having, diagnosed with, suspected of having, or at risk for developing a disease associated with exercise intolerance or endurance (e.g., rhabdomyolysis) or a subject in need of increased exercise endurance. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans. For example, the subject can be a human subject. The human subject can be a subject that uses exercise therapeutically. The human subject can be an athlete. An athlete can be any human subject that, either competitively or as a leisure activity, performs in athletic/exercise activities or sports (e.g., running).

Generally, a safe and effective amount of an S1P inhibiting agent is, for example, that amount that would cause the desired therapeutic effect in a subject while minimizing undesired side effects. In various embodiments, an effective amount of an S1P inhibiting agent described herein can substantially improve exercise tolerance or endurance.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of an S1P inhibiting agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to improve exercise tolerance or endurance.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of an S1P inhibiting agent can occur as a single event or over a time course of treatment. For example, an S1P inhibiting agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for improving exercise tolerance or endurance.

An S1P inhibiting agent can be administered simultaneously or sequentially with another agent, such as an antibiotic, an anti-inflammatory, or another agent. For example, an S1P inhibiting agent can be administered simultaneously with another agent, such as an antibiotic or an anti-inflammatory. Simultaneous administration can occur through administration of separate compositions, each containing one or more of an S1P inhibiting agent, an antibiotic, an anti-inflammatory, or another agent. Simultaneous administration can occur through administration of one composition containing two or more of an S1P inhibiting agent, an antibiotic, an anti-inflammatory, or another agent. An S1P inhibiting agent can be administered sequentially with an antibiotic, an anti-inflammatory, or another agent. For example, an S1P inhibiting agent can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts.

Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or regions of tissue. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening for S1P inhibiting agents.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: S1P Regulates Skeletal Muscle Function and Exercise Capacity

The following example describes the S1P regulation of skeletal muscle function and exercise capacity and that S1P is an effective target to improve exercise tolerance and cardiometabolic abnormalities in obesity.

Hypertension, dyslipidemia, and insulin resistance increase the risk of cardiovascular disease (CVD). These cardiometabolic abnormalities are common comorbidities in obese and type 2 diabetic (T2DM) patients, who are themselves at high risk for CVD and may be susceptible to a distinct cardiomyopathy characterized by left ventricular remodeling and dysfunction. Exercise is associated with improvements in cardiometabolic abnormalities common in obese and T2DM patients and obesity/diabetic rodent models. Moreover, physical activity correlates with improved outcomes in CVD and heart failure (HF). Regular physical exercise is beneficial for even healthy individuals, and is associated increased longevity. However, obesity, T2DM, and HF are associated with decreased exercise tolerance. Moreover, long-term adherence to a routine exercise regimen is difficult for many patients. Together, these observations underscore the importance of physical activity in patients at risk for CVD and the need for strategies that promote exercise tolerance and long-term adherence to an exercise program.

Site-1 Protease Ablation Increases Exercise Endurance

Site-1 Protease (S1P) is a Golgi-resident transmembrane domain protease required for the proteolytic cleavage and subsequent activation of several key transcription factors, most notably the sterol regulatory element-binding protein (SREBP) family and the unfolded protein response (UPR) regulator ATF6. When triggered by physiologic or pathophysiologic stimuli, S1P coordinates the adaptive response by activating transcription factors to turn on the expression of target genes that encode important components that regulate cellular homeostasis. For example, when cellular cholesterol levels are low, S1P cleaves SREBP2 to induce expression of enzymes in the cholesterol biosynthetic pathway. The role of the UPR in cellular stress is complex since its initial function is to improve ER folding capacity and restore ER homeostasis (which requires ATF6 activation); however if stress is prolonged and adaptation fails, this pro-survival signal can become pro-apoptotic leading to cell death. While the effects of S1P on cholesterol homeostasis and other key cellular functions have been extensively studied, the role of S1P in regulating skeletal muscle metabolism, physiology, and exercise endurance has not. It is presently believed that S1P plays an important role in regulating skeletal muscle mitochondrial metabolism and influencing the endurance for exercise.

Figure 9A:
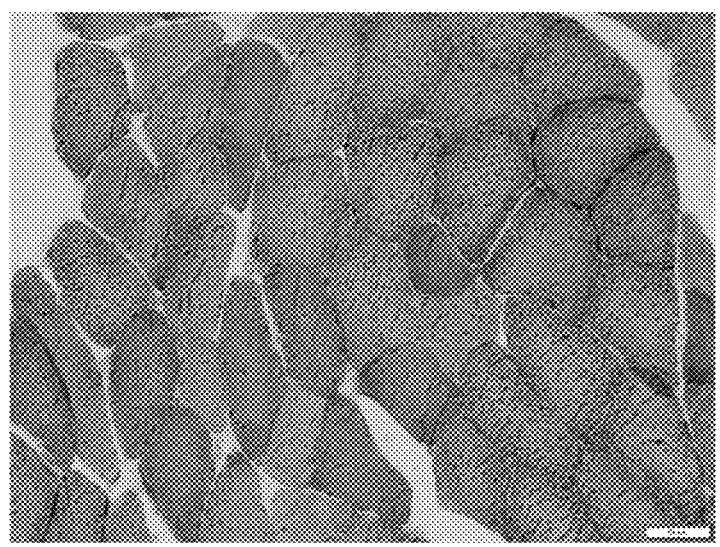
FIG. 9A-FIG. 9B is a series of images showing histological analysis of patient skeletal muscle. Patient muscle was stained as indicated and representative images are shown.
Figure 9B:
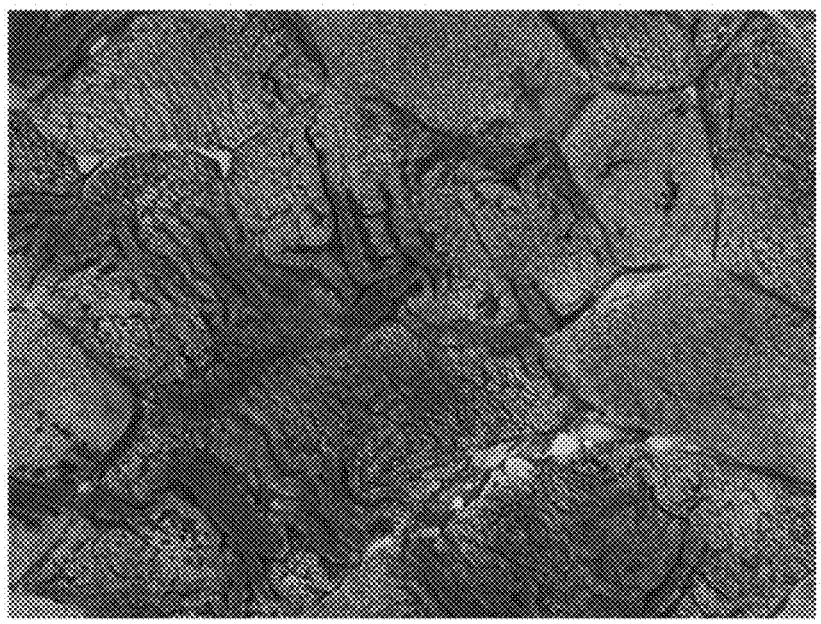

The inspiration for this stems from the recent identification of a patient heterozygous for a de novo mutation in S1P. Following even moderate physical activity, this patient exhibits marked muscle fatigue and idiopathic rhabdomyolysis with markedly elevated plasma creatine kinase (CK) and aspartate aminotransferase (AST) levels; indicative of dysfunctional muscle metabolism. Skeletal muscle biopsy revealed qualitatively enlarged mitochondria by electron microscopy (see e.g., FIG. 9A-FIG. 9B). Careful molecular analysis of this mutant has determined that the proline to serine mutation in the transmembrane domain causes mislocalization of S1P and results in increased S1P activity. Interestingly, as shown in the presently disclosed data, depletion of S1P in skeletal muscle (SM-S1P$^{KO}$) increases exercise tolerance and expression of markers of fatty acid oxidation after a single bout of exercise. Together, these observations support a novel function for S1P in skeletal muscle metabolism and exercise physiology, which has been little studied in that tissue. In the disclosed studies, a gap in the understanding of this topic will be addressed by characterizing the response of the SM-S1P$^{KO}$ mice to exercise and the metabolic pathways that are regulated by S1P in skeletal muscle.

The studies will identify the mechanism(s) by which S1P regulates skeletal muscle metabolism and exercise tolerance. Although S1P has not been directly linked to muscle metabolism and function, several S1P-regulated pathways have been suggested to have roles in exercise physiology. For example, ATF6 regulates the adaptation to exercise training, the SREBP target gene HMGCR is important for exercise tolerance, and the lysosome promotes exercise-induced clearance of dysfunctional mitochondria. While these are plausible connections, loss of function for each of those factors is associated with impaired exercise tolerance; the opposite of the phenotype that is observed with S1P deficiency.

Provided herein, is evidence that muscle of SM-S1P$^{KO}$ mice has a higher capacity for fatty acid oxidation, which could also be linked to enhanced exercise performance. It is presently believed that the exercise phenotype presently observed with loss of S1P is driven by enhanced mitochondrial metabolism in response to the exercise stimulus (see e.g., FIG. 1). The RNA-Seq and pathway analyses will allow the identification of patterns of gene expression that may point towards new substrates of S1P in skeletal muscle or compensatory pathways activated by S1P loss of function. In addition, the studies to examine training effects in diet-induced obese (DIO) SM-S1P$^{KO}$ mice will test if inhibition of S1P can also improve obesity-associated cardiometabolic abnormalities and enhance exercise tolerance; highlighting a use for S1P-targeted therapeutics. Indeed, S1P inhibitors have been developed (PF-42924231) and the feasibility of targeting this enzyme has been demonstrated in vivo.

In summary, it is presently believed these studies will show that S1P is a critical regulator of skeletal muscle metabolism and exercise endurance under both healthy and pathogenic conditions. Understanding this new function for S1P and its role in disease will expand the knowledge of human metabolic control and is of significance given the importance of exercise in cardiometabolic health.

Innovation

This example describes the examination of S1P regulation in skeletal muscle function and exercise endurance and show SP1 is an effective target to improve exercise tolerance and cardiometabolic abnormalities in obesity. While much work has explored the role of S1P in regulating diverse pathways involved in lipid metabolism, autophagy, viral susceptibility, and ER stress signaling, to date, a function for S1P in exercise endurance and skeletal muscle metabolism has not been reported. The generation of a mouse line with a skeletal muscle-specific depletion of S1P revealed a novel role for S1P in skeletal muscle metabolism and exercise endurance. The data indicates the exercise and metabolic benefits of inhibiting S1P do not require training, suggesting the SM-S1P$^{KO}$ mice have an enhanced ability to respond to an exercise challenge. The studies described herein can increase understanding of skeletal muscle function in health and disease and identify a novel role for S1P in skeletal muscle metabolism and exercise physiology.

Generation of skeletal muscle-specific S1P knockout mice (SM-S1P$^{KO}$)

Figure 2A:
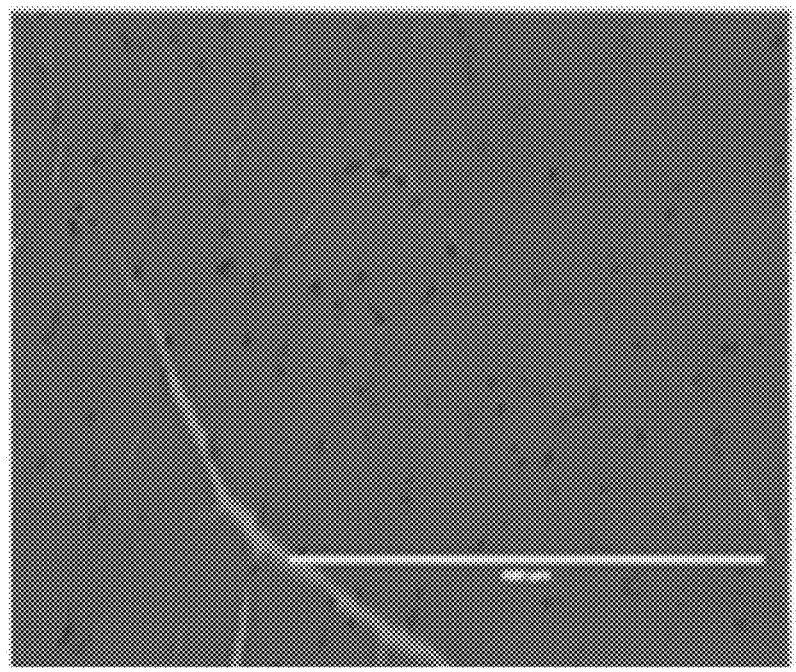
FIG. 2A-FIG. 2B is a series of images showing that muscle histology is normal in SM-S1P$^{KO}$ mice.
Figure 2B:
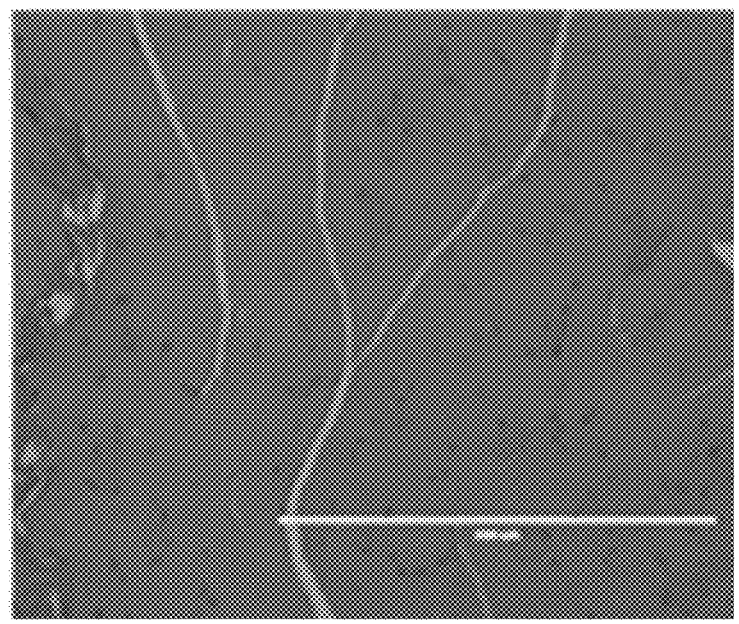
Figure 3A:
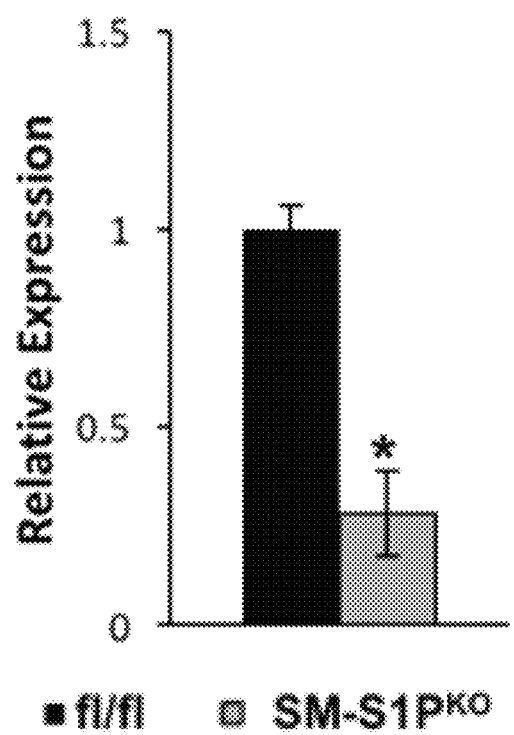
FIG. 3A-FIG. 3C is a series of bar graphs depicting measurements from sedentary SM-S1P$^{KO}$ mice compared to fl/fl control.
Figure 3B:
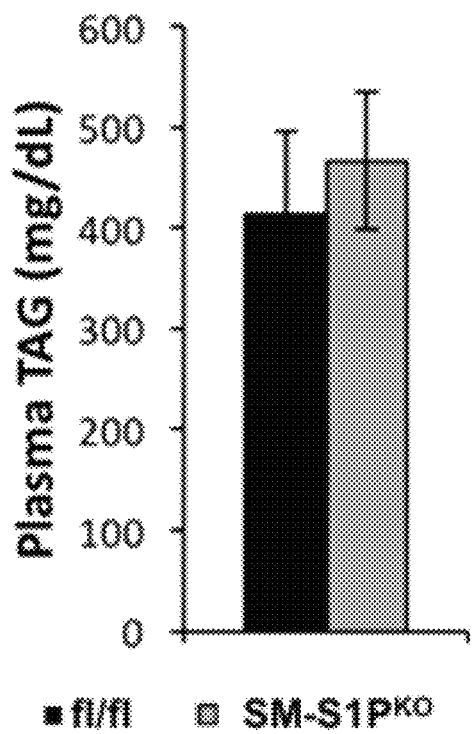
Figure 3C:
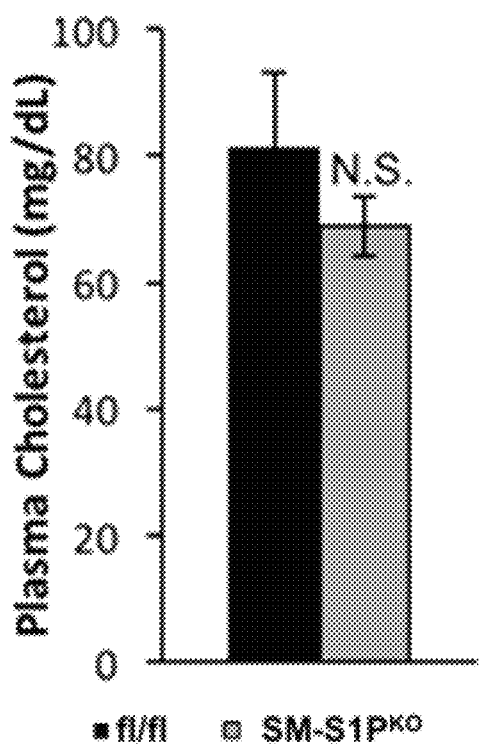

To investigate the role of S1P in metabolism and exercise, mice with skeletal muscle-specific S1P deficiency (SM-S1P$^{KO}$) were generated by crossing an established S1P floxed mouse line to mice expressing Cre recombinase driven by the human alpha-skeletal actin promoter (Jackson Labs). SM-S1P$^{KO}$ mice are born in the expected frequency relative to S1P floxed (WT) littermates, appear healthy, and have normal body weight and skeletal muscle structure, with no signs of myopathy by H&E staining (see e.g., FIG. 2). S1P mRNA levels are reduced in the gastrocnemius of SM-S1P$^{KO}$ mice (see e.g., FIG. 3A). Plasma triacylglycerol (TAG) and cholesterol levels are normal in fasted SM-S1P$^{KO}$ mice compared to fasted WT littermates (see e.g., FIG. 3B-FIG. 3C).

In summary, a SM-S1P$^{KO}$ mouse line generated was overtly healthy and displays normal TAG and cholesterol levels.

Figure 4A:
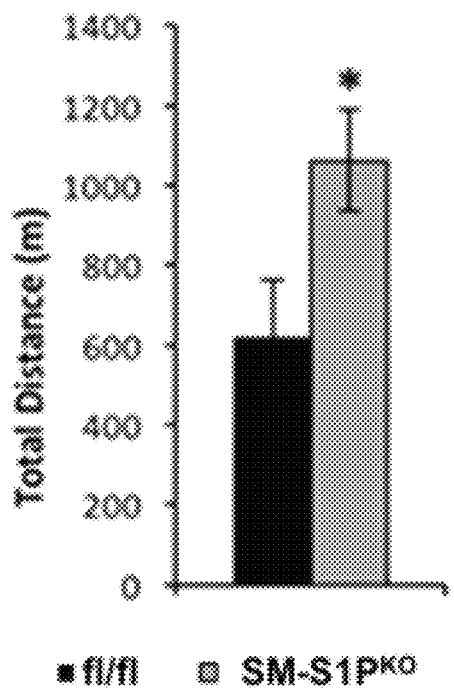
FIG. 4A-FIG. 4C is a series of bar graphs showing that SM-S1P$^{KO}$ mice have enhanced exercise endurance.
Figure 4B:
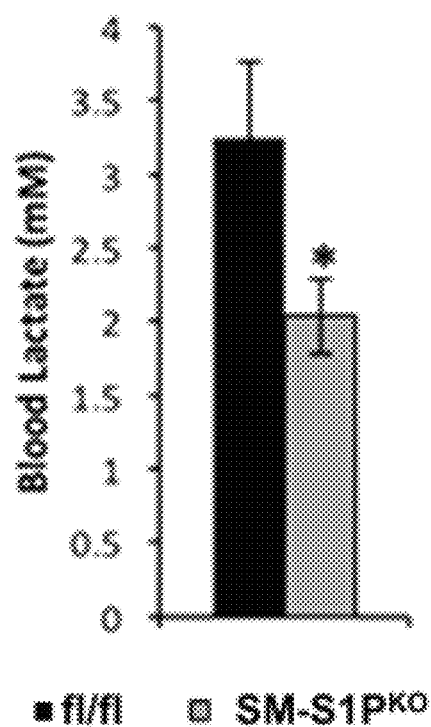
Figure 4C:
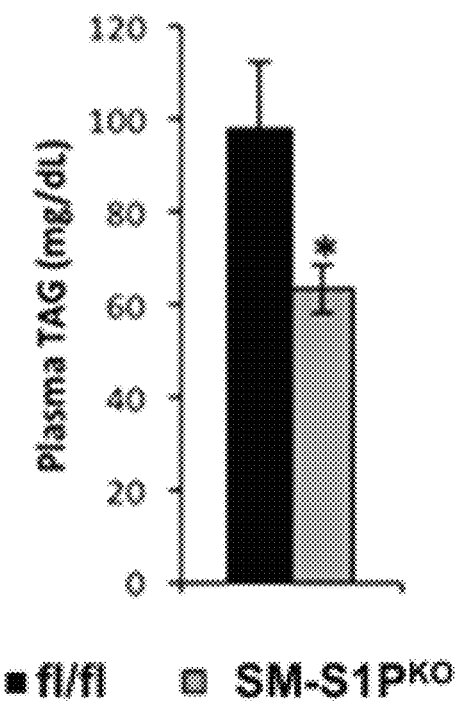

SM-S1P$^{KO}$ Mice Display Enhanced Exercise Tolerance and Elevated Fatty Acid Oxidation Gene Expression Because an S1P gain-of-function mutation was associated with exercise intolerance, the exercise performance of the SM-S1P$^{KO}$ mice was investigated by subjecting the mice to a single bout of a graded exercise test to exhaustion via treadmill. SM-S1P$^{KO}$ mice display enhanced exercise tolerance during a single bout of exercise compared to WT littermates (see e.g., FIG. 4A). Blood lactate and plasma TAG levels were decreased in SM-S1P$^{KO}$ mice immediately following exercise (see e.g., FIG. 4B-FIG. 4C). This observation suggests that fatty acid oxidation is enhanced in the skeletal muscle of these mice.

Figure 5:
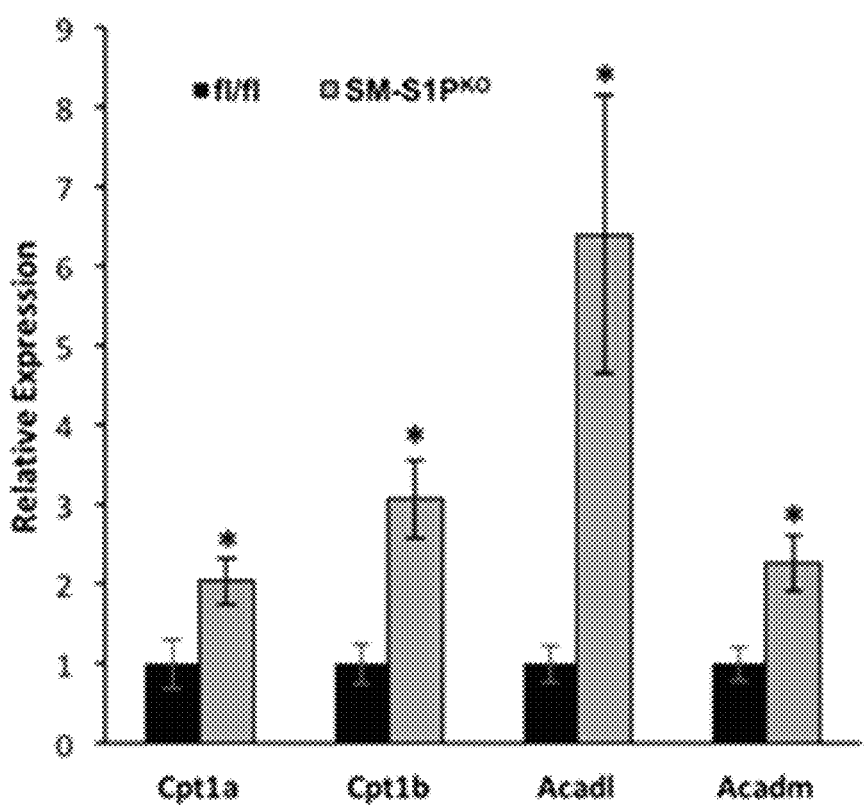
FIG. 5 is a bar graph showing that SM-S1P$^{KO}$ mice exhibit elevated expression of mitochondrial biogenesis and fatty acid oxidation genes. Gene expression in the soleus immediately after exercise. n=5-6, *p<0.05. Mice fasted 4 h prior to exercise.

Consistent with this, qRT-PCR analysis showed elevated expression of genes encoding enzymes involved in fatty acid metabolism (Cpt1a and b, Acadl, and Acadm) (see e.g., FIG. 5). These data suggest fat utilization may be enhanced during exercise in SM-S1P$^{KO}$ mice. This could constitute an energetic advantage over WT mice and explain the enhanced exercise performance of the SM-S1P$^{KO}$ mice. The studies outlined in section (I) will provide further evidence confirming fatty acid oxidation is increased by conducting more rigorous metabolic studies, determining other aspects of intermediary metabolism that can be affected, and identifying the mechanism(s) by which loss of S1P may be altering metabolism.

Figure 6:
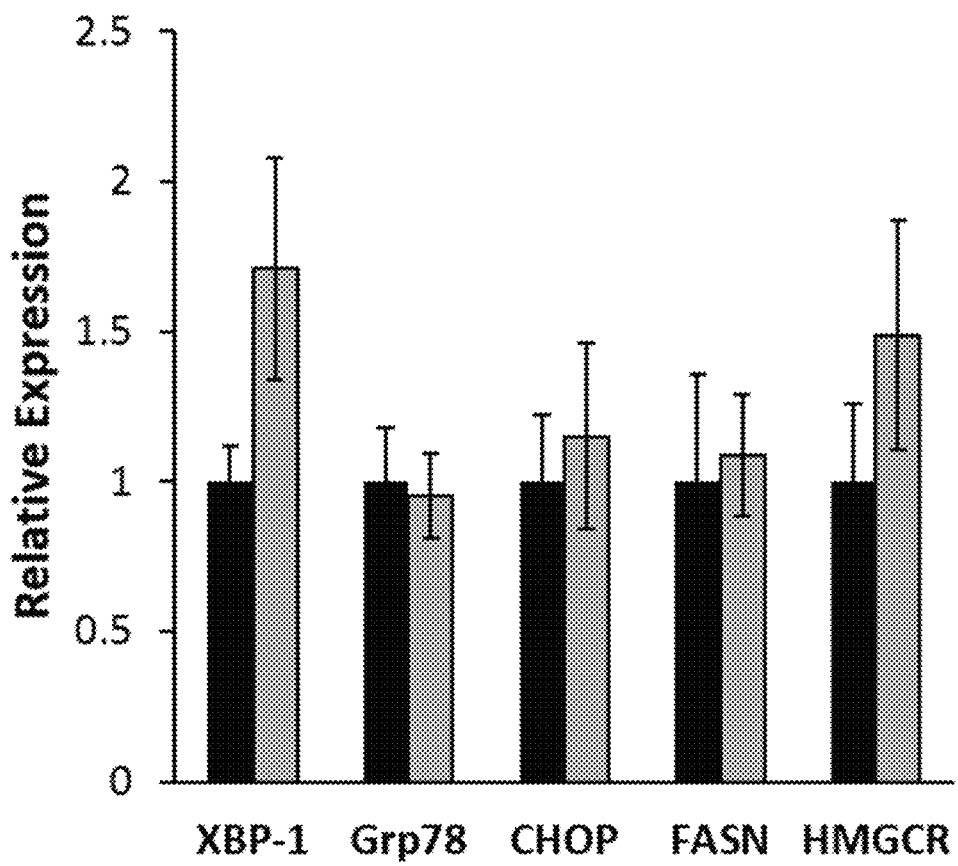
FIG. 6 is a bar graph showing that UPR and SREBP target gene expressions are unchanged in SM-S1P$^{KO}$ after exercise. Gene expression in the soleus immediately after exercise n=5-6. Mice fasted 4 h prior to exercise.

Activation of UPR and SREBP signaling in exercised SM-S1P$^{KO}$ skeletal muscle was also examined. Expression of key UPR and SREBP target genes were similar between exercised SM-S1P$^{KO}$ mice and exercised controls (see e.g., FIG. 6), suggesting S1P depletion in skeletal muscle does not alter these pathways in response to acute exercise.

Together these data provide evidence that depletion of S1P in skeletal muscle enhances fatty acid utilization and promotes exercise tolerance, potentially via a UPR- and SREBP-independent mechanism.

(I) Characterize Skeletal Muscle Metabolism in Sedentary and Exercised SM-S1P$^{KO}$ Mice It is believed that fatty acid oxidation and exercise tolerance are enhanced in exercised SM-S1P$^{KO}$ mice.

The data suggests SM-S1P$^{KO}$ mice have increased exercise endurance, with decreased blood lactate and TAG concentrations post-exercise. This is accompanied by increased expression of genes encoding enzymes involved in fatty acid metabolism. The studies will confirm these findings and determine whether S1P is a regulator of fatty acid and glucose utilization in skeletal muscle. These studies will also establish a role for S1P in exercise physiology.

12-week old male and female SM-S1P$^{KO}$ mice and their floxed (WT) littermates will be used. Mice will be fasted for 4 h, and then randomly assigned into two groups: (1) sedentary or (2) exercised. Because changes in gene expression may not immediately translate to altered metabolism, mice at t=0 h, 6 h, and 24 h post-exercise will be examined for gene expression/Western blot, mitochondrial oxidation, and plasma chemistry endpoints. For exercised and sedentary mice, plasma will be harvested and tissues snap-frozen in liquid nitrogen or embedded in O.C.T. compound and snap-frozen in isopentane at sacrifice. For the tissue and plasma analysis below, sedentary and exercised WT and SM-S1P$^{KO}$ mice will be compared.

These studies will also be performed on wild-type mice treated with the highly selective S1P inhibitor PF-429242 or vehicle, to validate the mouse model, provide scientific rigor by using a complimentary approach, and assess the therapeutic potential of pharmacologic S1P inhibition on exercise endurance and skeletal muscle metabolism. Initial dosage and treatments will be based on PF-429242 in vivo mouse studies showing 30 mg/kg i.p. injection of PF-429242 every 6 hrs for 24 hr effectively inhibits S1P in mouse liver. This regimen will be adjusted as needed to optimally inhibit S1P in skeletal muscle of wild-type mice (see e.g., Example 3).

Exercise endurance: Mice will undergo a single bout of a graded exercise test to exhaustion using a 4-lane treadmill on a 0% incline, with an electric grid at the back of each treadmill. Three days before the endurance test, mice will have 3 days of acclimation at 10 m/min at 0% incline for 5 min. The test will involve a 5 min acclimation period on the treadmill (turned off), followed by: 5 m/min for 5 min; 10 m/min for 5 min; 15 m/min for 10 min; 25 m/min for 10 min; and finally, 30 m/min until exhaustion is reached. Exhaustion is defined as the inability of the mouse to resume running within 10 s after direct contact on the electric grid and inability to right itself when placed on its back.

Body composition, food intake, activity, and indirect gas calorimetry: Body composition (lean mass and fat mass) will be measured. A single-lane enclosed treadmill fitted with a computerized gas calorimetry measurement system (Columbus Instruments) will be used to quantify oxygen consumption and $CO_2$ production during a graded high intensity exercise test to exhaustion. Respiratory exchange ratio (RER) values will be calculated from the indirect calorimetry values. Mice will be acclimated to the treadmill prior to being assessed; average values of each parameter will be calculated after acclimation.

In vivo long-chain fatty acid (LCFA) and glucose uptake: The right jugular vein and left carotid artery will be surgically catheterized and mice recovered for 1 week. In vivo uptake studies will be after a 4 h fast using VMMPC established protocols. Mice will be acclimated to the treadmill via a single 10 min bout at 13 m/min (0% incline) 2 days before. From −60 to 0 min, mice will be placed on a treadmill while off to acclimate. At t=0 min, arterial blood will be sampled to measure glucose, hematocrit (Hct), lactate, insulin, and NEFAs. Remaining erythrocytes will be heparin-saline-washed and reinfused to prevent a fall of >5% Hct. Mice will either remain sedentary with the treadmill off or be exercised on the treadmill at 16m/min (0% incline). At t=5 min, all mice will be infused with a bolus of 2[$^{14}$C]deoxyglucose (2[$^{14}$C]DG, 13 µCi) and [9,10-$^3$H]-(R)-2-bromopalmitate ($^3$H-R-BrP; 26 µCi) to measure tissue-specific glucose and LCFA uptake and clearance. Arterial blood will be sampled at t=7, 10, 15, and 20 min to determine glucose, lactate, NEFAs, 2[$^{14}$C]DG, and $^3$H-R-BrP. At t=30 min, a larger blood sample (−150 µl) will be taken to measure glucose, Hct, lactate, insulin, NEFAs, 2[$^{14}$C]DG, and $^3$H-R-BrP. After sacrifice, soleus, gastrocnemius, and superficial vastus lateralis will be harvested to assay for phosphorylated 2[$^{14}$C]DG (2[$^{14}$C]DG-P) and $^3$H-R-BrP.

Tissue and ex vivo endpoints: To be performed in slow twitch type I (soleus) and fast twitch type II (extensor digitorum longus (EDL)) muscles to fully characterize S1P function in skeletal muscle.

Plasma chemistries: Tail blood glucose and lactate will be determined using a Contour Next EZ glucometer (Bayer) and a Lactate Plus lactate meter (Nova Biomedical), respectively, immediately before sacrifice. CK, alanine aminotransferase (ALT), AST, insulin, TAG, free fatty acids, and ketones will be assessed in plasma collected at sacrifice using colorimetric and enzymatic assays or ELISAs as reported.

Gene expression: Expression of genes encoding mitochondrial fatty acid oxidation enzymes (Cpt1a and b, Acadl, Acadm, Fgf21, etc.), fatty acid transporters (CD36, FABP3), glucose transporters (Glut4), glycolytic enzymes (HKII, Gck), glucose oxidation enzymes (Mpc1 and 2, Pdk4), electron transport chain (Cox2, Citc, etc.), and regulators of mitochondrial biogenesis (PGC-1α, NRF1 and 2, etc.) will be assessed in soleus, EDL, and gastrocnemius muscles by qRT-PCR. Mitochondrial DNA (mtDNA) content (ND1 DNA abundance) will be quantified and normalized to nuclear DNA (GAPDH DNA) abundance. S1P pathways such as the expression of SREBP1/2 target genes will be examined and analysis of ATF6 gene targets will be completed. Markers of necrosis, inflammation, and regeneration will also be examined.

RNA-Seq and pathway analyses will also be performed to capture the global transcriptional impact of S1P-deletion on skeletal muscle. This approach will potentially identify patterns of gene expression that will point us towards new S1P substrates in skeletal muscle. RNA-Seq will be performed. RNA-Seq results will be validated by qRT-PCR and Western blotting.

Western blotting: Protein levels of mitochondrial electron transport chain complexes and PGC-1α, will be assessed in soleus and EDL muscles. mRNA changes in fatty acid oxidation enzymes will be confirmed by Western blot analyses. AMPK is a regulator of fatty acid utilization and glucose transport during exercise, thus to determine whether AMPK is differentially regulated in SM-S1P$^{KO}$ mice, the abundance of phosphorylated and total AMPK and ACC proteins in soleus and EDL will be examined. Levels of proteins associated with metabolic pathways suggested by the presently described metabolomics studies below will be assessed.

Metabolomics: Untargeted metabolomics using LC-MS will be performed as reported previously on soleus and EDL of SM-S1P$^{KO}$ mice and WT littermates to identify metabolic alterations associated with S1P depletion in sedentary and exercised mice. Post-exercise timepoint(s) tested will be determined by gene expression/WB and mitochondrial oxidation studies.

Fiber-type distribution and histology/ultrastructure: Distribution of fiber-types of the plantar flexion (i.e., soleus, gastrocnemius, and plantaris) will be determined in sedentary and exercised SM-S1P$^{KO}$ and WT mice by immunofluorescence using appropriate antibodies to detect myosin heavy chain type I, IIA, IIB, and IIX. General histological analysis of H&E stained EDL and soleus sections will be performed to detect alterations in skeletal muscle structure in SM-S1P$^{KO}$ mice. Skeletal muscle ultrastructure of EDL and soleus will be visualized by electron microscopy using a JEOL JEM-1400Plus TEM.

Ex-vivo whole muscle stimulation: Contractile function and fatigability will be assessed using established techniques. Mice will be continuously anesthetized with 2% inhaled isoflurane at 2 L/min and either the 5$^{th}$ toe muscle of the EDL or soleus muscle will be isolated and mounted in a specialized muscle chamber containing Ringers solution with 10 mg/L curare. Within the chamber, the tendon of insertion will be secured at the musculotendonous junction via 8-0 suture to a dual mode ergonometer, while the tendon of origin is similarly secured to a rigid post. Muscle activation will be provided by parallel plate electrodes flanking the muscle. Optimal muscle length will be determined and a twitch contraction will be elicited followed by an isometric tetanic contraction. A force-frequency relationship will be determined eliciting contractions at increasing frequencies. Muscle fatigability will be evaluated by eliciting repeated tetanic contractions. Time to fatigue will be determined as the time it takes each muscle to fall to 60% of the maximal developed force. All forces will be normalized to muscle physiological cross-sectional area.

Mitochondrial oxidation: High resolution respirometry of permeabilized soleus and EDL muscles will be conducted using a 2-chamber Oxygraph O$^2$K (OROBOROS Instruments). Respiratory substrates will include: pyruvate/malate, palmitoyl-carnitine, glutamate/malate, and succinate plus rotenone. After substrate addition and measurement of basal respiration, maximally-stimulated respiration by addition of ADP will be measured. Activities of mitochondrial complexes I, II+III, and IV and citrate synthase will be measured in soleus and EDL homogenates using spectrophotometric enzyme assays.

It is believed that the skeletal muscle-specific depletion of S1P enhances exercise endurance and increases fatty acid oxidation during exercise as evidenced by: increased expression of fatty acid oxidation enzymes, enhanced fatty acid oxidation in muscle, a reduction in the RER value, and increased LCFA muscle uptake in exercised SM-S1P$^{KO}$ mice compared to exercised WT littermate controls. The muscle glucose uptake outcomes will be measured in these mice, significant differences in carbohydrate metabolism genes have not been detected, but the lactate levels were lower in the SM-S1P$^{KO}$ mice and the rigor and power of this technique will provide informative data about glucose usage in SM-S1P$^{KO}$ muscle.

The data show normal expression of components of the UPR pathway, targets of SREBP, and lysosomal function in muscle of the SM-S1P$^{KO}$ mice, suggesting that these pathways are not under the control of S1P in skeletal muscle. The idea that the effects of S1P loss of function on exercise performance is not due to its effects on canonical partners is also supported by what is known about the effects of inhibiting these other pathways, which is the opposite of what has been observed in SM-S1P$^{KO}$ mice, here. This also suggests that the SM-S1P$^{KO}$ phenotype is mediated through other (perhaps novel) S1P substrates. These untargeted metabolomics and RNA-Seq studies will identify metabolic pathways and uncover patterns of gene expression that will point us towards new S1P substrates or effects on other pathways known to affect exercise endurance (e.g., glycogen metabolism, angiogenesis, etc.).

These studies could then be extended to examine the effects of this new substrate on intermediary metabolism.

Successful acute PF-429242 treatment in vivo has been reported. PF-429242 may reach organs beyond skeletal muscle, potentially producing alternative effects. Despite these potential shortcomings, it is believed that S1P genetic (SM-S1P$^{KO}$) and pharmacologic inhibition will show the same effects on metabolism and exercise. This would also d robustly demonstrate a function for S1P in this context.

(II) Determine the Effects of S1P on Cardiometabolic Abnormalities Associated with Diet-Induced Obesity in Sedentary and Exercise-Trained Mice It is presently believed S1P depletion in skeletal muscle will improve obesity-associated cardiometabolic outcomes and left ventricular (LV) function in exercise-trained high-fat diet (HFD) fed SM-S1P$^{KO}$ mice compared to HFD exercise-trained VVT mice and sedentary HFD SM-S1P$^{KO}$ nd WT mice.

The presently described data show SM-S1P$^{KO}$ mice have increased exercise endurance, elevated markers of fatty acid oxidation, and decreased serum TAG levels, after only a single bout of exercise. Exercise training is associated with improved fatty acid oxidation and cardiometabolic outcomes. These studies coupled with the presently disclosed data suggest exercise training will further enhance the exercise and metabolic phenotypes observed in the SM-S1P$^{KO}$ mice.

Obesity-associated cardiometabolic abnormalities (i.e., insulin resistance, hypertension, elevated serum lipid levels) are improved by exercise. In HFD fed mice, exercise training results in decreased body weight, lowered plasma TAG and cholesterol, improved glucose tolerance, restored insulin sensitivity, decreased skeletal muscle lipid accumulation, and improved. It is believed that SM-S1P$^{KO}$ mice will exhibit enhanced cardiometabolic outcomes and ventricular functional benefit in response to exercise training compared to WT mice. These studies will further address the combined therapeutic benefit of S1P inhibition and exercise to improve cardiometabolic outcomes in obesity.

Six-week-old SM-S1P$^{KO}$ male mice and WT male littermates will be placed on a diet enriched with fat (45% Kcal; HFID, Research Diets Inc., catalog #D12451) that has been shown to cause obesity and insulin resistance or a low fat (6.5% Kcal) control diet (LFD; Purina Formulab Diet 5008). After 4 weeks, LFD and HFD mice will be divided into (1) sedentary and (2) exercise-trained groups designated as LFD-sedentary; LFD-trained; HFD-sedentary; and HFD-trained for SM-S1P$^{KO}$ and WT genotypes. Mice will be housed individually with either a functional running wheel (for exercise-trained groups) or a locked, non-functional running wheel (for sedentary groups) for 6 weeks, as described previously. Body weight and blood glucose and lactate levels will be checked weekly. Wheel running activity will be continuously recorded (Columbus Instruments) for 6 weeks. Running episodes lasting longer than 10 s will be used to calculate total distance covered and running velocity. The benefits of voluntary wheel running on metabolic readouts in HFD mice are well known. If SM-S1P$^{KO}$ mice inherently run more than WT littermates it would impact the studies. Therefore, first a voluntary wheel running pilot study on CHOW-fed SM-S1P$^{KO}$ and WT littermates will be performed to determine if voluntary wheel running differs between genotypes. If differences exist, forced treadmill training will be used instead for the training studies.

Mice will undergo metabolic testing or be sacrificed for tissue and plasma harvest after a 4 hour fast. Muscle, heart, liver, gonadal, and subcutaneous fat tissue samples will be frozen in liquid nitrogen and stored at −80° C. or fixed in 10% formalin or embedded in O.C.T. compound and snap-frozen in isopentane.

The following in vivo and ex vivo endpoints will be performed on sedentary LFD and HFD and exercise-trained LFD and HFD mice for both SM-S1P$^{KO}$ and WT genotypes (4 mouse groups total).

In vivo endpoints include: Exercise endurance, body composition, food intake, activity, and indirect gas calorimetry: Will be performed as described in section (I).

Glucose tolerance test and Hyperinsulinemic-euglycemic clamp: GTT: After a 6 hour fast, mice will receive an intraperitoneal injection of glucose (1 g/kg body weight). Blood glucose concentrations will be measured from tail vein blood samples using a blood glucose meter (Contour Next EZ glucometer, Bayer) starting at t=0 min and at 15, 30, 60, 90, and 120 min post glucose injection. The right jugular vein and left carotid artery will be surgically catheterized and mice recovered for 1 week. After a 5 hour fast, hyperinsulinemic clamp studies will be performed on conscious mice using the protocol established at the VMMPC. At t=−90 min a primed-continuous infusion of HPLC-purified [3-$^3$H]-glucose will begin and be maintained throughout the experiment. Euglycemia (~9 mmol/l) will be maintained by measuring blood glucose every 10 min starting at t=0 min and infusing 50% dextrose as necessary. Additional blood will be taken at t=80, 90, 100, 110, and 120 min and processed to determine plasma [3-3H] glucose. A 12-µCi bolus of [2-14C] deoxyglucose ([2-$^{14}$C]DG) will be given at t=120 min. Blood samples will be obtained at t=122, 135, 145, and 155 min and processed to determine plasma [2-14C]DG. Mice will receive saline-washed erythrocytes from donors beginning at t=0 min and continuously throughout the clamp to prevent a fall of >5% Hct. Rate of glucose infusion will also be determined.

LV function and cardiac stress test will be determined. Adult mice will be anesthetized with Isoflurane (2% maintenance)+pancronium (1 mg/kg given once) to provide a surgical plane of anesthesia and allow a normal heart rate of 400-500 beats/min without breathing artifacts. Mice will be intubated and ventilated with a Harvard ventilator set at 200-400 µl. The right carotid will be cannulated with a 1.4 Fr Scisense catheter that will be advanced into the right carotid, into the ascending aorta, and across the valve retrograde into the left ventricle. In these animals, functional data will be acquired at baseline and in response to increasing doses of dobutamine to produce a pharmacologic cardiac stress test. Previous work has shown impaired ionotropic response to dobutamine in HFD mice. Echocardiograms can also be performed, but this course of dietary intervention does not generally result in systolic or diastolic dysfunction without ionotropic stimulus.

Tissue and ex vivo endpoints include: plasma chemistries performed as described in section (I). Additionally, skeletal muscle and liver TAG and glycogen levels will be measured at sacrifice by colorimetric and enzymatic assays, respectively.

Gene expression: Expression of genes and proteins and pathways identified by the RNA-Seq studies or delineated in section (I) will be examined in the context of DIO to determine whether these targets are associated with obesity-associated cardiometabolic abnormalities and reduced exercise endurance. Whether S1P expression and its target pathways are altered by DIO and/or exercise training will also be examined.

Skeletal muscle and cardiac mitochondrial oxidation will be performed as described in section (I) with permeabilized soleus and EDL muscles and isolated cardiac mitochondria.

LFD exercise trained mice: Based on the data, it is believed that exercise training will enhance exercise tolerance and fatty acid oxidation in trained LFD-SM-S1P$^{KO}$ mice compared to trained LFD-WT littermates, and will surpass the enhancements seen in the single-bout exercised SM-S1P$^{KO}$ mice in section (I).

HFD exercise trained mice: Based on the data, it is believed that HFD-trained SM-S1P$^{KO}$ mice will have increased exercise tolerance, decreased body weight, improved insulin sensitivity and glucose tolerance compared to HFD-trained WT littermates. It is also believed HFD-trained SM-S1P$^{KO}$ mice will show decreased lipid accumulation in skeletal muscle and liver compared to HFD-trained WT littermates. It is also believed that HFD-trained SM-S1P$^{KO}$ mice will exhibit improved contractile response (higher dP/dtmax) and cardiac relaxation response (dP/dtmin) in response to dobutamine compared to HFD-sedentary mice (SM-S1P$^{KO}$ and WT littermates). If increased exercise tolerance of SM-S1P$^{KO}$ persists or is further improved by training, then it is believe ventricular functional improvements in HFD-trained SM-S1P$^{KO}$ may surpass those of HFD-trained WT littermates. If these improvements are observed in response to genetic deletion, the therapeutic effects of PF-429242 versus vehicle in HFD-trained and HFD-sedentary wild-type mice will be tested.

The mechanisms of S1P function at play in the SM-S1P$^{KO}$ mice may also be applicable in a cardiac-specific S1P$^{KO}$ mouse line and may help to identify new therapeutic targets for CVD.

HFD is associated with incomplete β-oxidation and accumulation of β-oxidative intermediates. Beneficial outcomes observed in SM-S1P$^{KO}$ mice may be a result of improved β-oxidation in the face of HFD (as shown for mice with elevated PGC-1α expression, which the CHOW-fed SM-S1P$^{KO}$ mice exhibit, data not shown).

Sedentary LFD and HFD mice: Based on the data, it is believed that S1P function in skeletal muscle metabolism and exercise is adaptive, thus sedentary SM-S1P$^{KO}$ mice will be indistinguishable from sedentary WT littermates regardless of LFD or HFD, based on the presently disclosed data (see e.g., FIG. 2-FIG. 3). Based on the present data, it is believed that both knockout and LFD-WT mice will have better cardiometabolic endpoints, LV function, and mitochondrial oxidation compared to HFD regardless of genotype. Sedentary SM-S1P$^{KO}$ mice may have improved endpoints compared to sedentary WT mice (i.e., less weight gain on HFD, improved glucose/insulin tolerance and LV function), in which case, the role of S1P as an innate driver of skeletal muscle and multi-organ metabolism will be investigated.

Training may alter levels of S1P; however, in the single bout WT exercised mice, S1P mRNA levels remained unchanged (data not shown). If changes are detected in S1P expression (either mRNA and/or protein) in trained WT mice, the mechanism(s) responsible will be investigated.

Example 2: A Mutation in Site-1 Protease is Associated with a Complex Phenotype

The following example describes the discovery of a critical function for S1P in several human organ systems and implicate an important role for S1P in various human disease states. Described herein is the discovery of a mutation in Site-1 Protease that is associated with a complex phenotype that includes episodic hyperCKemia and focal myoedema.

Abstract

Background: Site-1 Protease (S1P) is a Golgi-resident protein required for the activation of regulatory proteins that drive key cellular functions, including, the unfolded protein response (UPR) and lipid and cholesterol biosynthesis. While disruptions in S1P function have been widely characterized in animal models, to date, the implications of disrupted S1P function in human disease states are not completely known.

Figure 7:
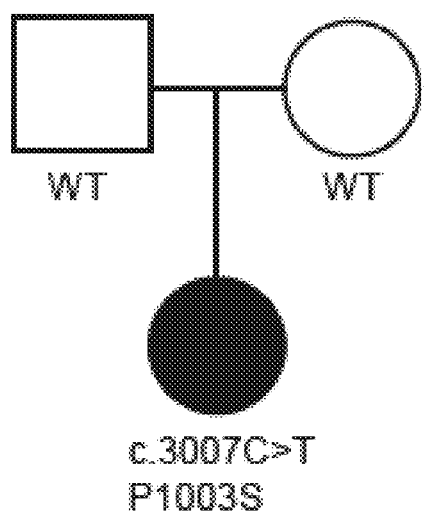
FIG. 7 is a patient pedigree chart, denoting the de novo c.3007C>T mutation, which was revealed by whole exome sequencing.

Methods: The patient and both parents underwent whole exome and mitochondrial DNA sequencing, and Sanger sequencing was used to confirm the mutation. See FIG. 7 for a pedigree chart. Western blotting and immunofluorescence studies were performed on either proband-derived fibroblasts or on an established cell line to assess protein expression and cellular localization of the mutated S1P protein. Quantitative real-time PCR and luciferase reporter assays were used to examine activation of S1P target pathways in the context of the S1P mutation.

Results: A female patient is described with a de novo heterozygous missense mutation in the transmembrane domain of S1P (p. Pro1003Ser). The patient presented to a neuromuscular clinic with episodic, activity-induced, focal myoedema and myalgias with hyperCKemia. Her clinical phenotype was complex and included gastrointestinal hypomotility, ocular migraines, and polycystic ovary syndrome. Molecular analysis using proband-derived fibroblasts and cell lines harboring the Pro1003Ser mutation demonstrated increased activation of UPR and lipid and cholesterol regulatory pathways and localization of S1P Pro1003Ser in the Golgi.

Conclusion: These findings suggest a critical function for S1P in several human organ systems and implicate an important role for S1P in various human disease states.

Introduction

Site-1 Protease (S1P; also known as subtilisin/kexin-isozyme 1 or PCSK8) is a membrane-bound serine protease required for the activation of key regulators of cellular functions, most notably, the unfolded protein response (UPR), lysosomal biogenesis, and lipid and cholesterol biosynthesis. Disruptions in these cellular functions are implicated in several human diseases and restoring their normal function is a common therapeutic focus. S1P is encoded by the MBTPS1gene (OMIM accession number 603355) and exists as an inactive precursor in the endoplasmic reticulum (ER). After a series of autocatalytic cleavage events, the mature S1P localizes to the Golgi where it can proteolytically cleave its substrates, the most well-known being the sterol regulatory element-binding protein family (SREBPs) of transcription factors, essential regulators of lipid and cholesterol homeostasis, and ATF6, a component of the UPR required to restore ER homeostasis.

Many animal studies suggest an important role for S1P in developmental, physiologic, and pathogenic functions. These observations along with S1P's regulation of signaling pathways involved in insulin resistance, nonalcoholic fatty liver disease, and persistent viral infection has made S1P the focus of pharmacological development efforts. While these animal studies underscore an important role for S1P in health and disease, to date, the impact of S1P disruption on human health is not clearly understood.

Herein is described a 24-year old female patient with a novel heterozygous de novo mutation in MBTPS1 (NM_003791.3 c.3007C>T) that corresponds to a mutation in the highly conserved transmembrane domain of S1P (NP_003782.1 p. Pro1003Ser). The mutated MBTPS1 transcript is expressed at levels similar to the wild-type transcript. The patient exhibited a complex phenotype suggestive of disrupted metabolism that includes muscle fatigue and hyperCKemia precipitated by moderate physical activity. Additional clinical complications include ovarian cysts, small fiber neuropathy, and chronic constipation. Functional analysis of the mutant protein indicates Golgi localization of the protein and increased activation of its target pathways.

Methods

Whole Exome and Mitochondrial DNA Sequencing

Exome sequencing was performed by GeneDx (Gaithersburg, Md.) using Agilent SureSelect XT2 All Exon V4 Kit and Illumina HiSeq 2000 100 bp paired-end reads. Sequence was aligned to the UCSC build hg19 reference sequence. Mean depth of coverage of known protein-coding RefSeq genes was 89× with a quality threshold of 97.9%. For the MBTPS1 gene (gDNA NG_033017.1, cDNA NM_003791.3), 94.1% of the coding region was covered at a minimum of 10× by exome sequencing. GeneDx's XomeAnalyzer was used to evaluate sequence changes between the proband, parental samples, and reference. Sanger sequencing was used for confirmation of the reported mutation.

Transcript Characterization

Genomic DNA and RNA were extracted from patient and healthy donor fibroblasts using RNA-Bee (Tel-Test, Inc.) and cDNA was synthesized from RNA using SuperScript III (Invitrogen). To assess possible allele-specific expression of the c.3007 mutant allele, sets of PCR primers were designed that would amplify a genomic DNA or cDNA region that includes the MBTPS1 c.3007C>T variant. The genomic DNA primers were located in adjacent introns, while the cDNA primers were located in adjacent exons, spanning two exon-exon junctions. Both the genomic and cDNA-derived PCR products were sequenced on an Applied Biosystems 3130xl capillary sequencer and the Sanger trace files were compared with Applied Biosystems Sequence Analysis software. Illumina adaptors were ligated onto the ends of the patient and control cDNA-derived PCR products and deep next-generation sequencing was performed using an Illumina Miseq instrument (Illumina).

Cell Culture

All cells were maintained at 37° C. with 5% $CO_2$. Primary skin fibroblasts were derived from patient and healthy donor skin biopsies. Human fibroblasts were cultured in high-glucose DMEM supplemented with 10% fetal bovine serum (FBS) and 1% penicillin-streptomycin (PS). Patient and donor fibroblasts were used at matched passage numbers no greater than passage 10. The S1P-deficient SRD-12B cell line was maintained in Medium B (DMEM/F12, 5% FBS, 1% PS, 5 μg/ml cholesterol, 1 mmol/L sodium mevalonate, 20 μmol/L sodium oleate). Medium A (DMEM/F12, 1% PS) was supplemented with 5% lipoprotein-deficient serum (LPDS) where indicated.

Cell Growth Assay

On Day 0, SRD-12B cells were plated in 6 $cm^2$ dishes at $2\times10^5$ in Medium B, transfected using Lipofectamine 2000 (Invitrogen) with wild-type S1P, S1P Pro1003Ser, or empty vector on Day 1, and shifted to Medium A with 5% LPDS on Day 2. Medium was changed every two days and on Day 7, cells were rinsed in PBS, fixed in ice-cold methanol at −20° C., and stained with 5% crystal violet.

Luciferase Reporter Assay

On Day 0, SRD-12B cells were plated in 12-well plates at 50% confluency in Medium B. On Day 1, wells were transfected in quadruplicate using 3 μl FuGENE HD (Promega), 50 μl Optimem Media (Gibco), 1.25 μg FAS-Luc, 0.12 μg *Renilla*, and either 0.25 μg wild-type S1P or S1P Pro1003Ser constructs per well. After 9-10 hr, cells were washed twice with 1×PBS and fed DMEM/F12 for 16 hr. Luciferase activities were then measured using the Promega Dual-Glo Luciferase Assay kit and the ratio between firefly and *Renilla* luciferase activities was determined.

Immunofluorescence

Human skin fibroblasts were transfected using Lipofectamine 2000 with either wild-type S1P or S1P Pro1003Ser constructs. After 24 hr, cells were fixed in paraformaldehyde and incubated with anti-FLAG, anti-KDEL, and anti-GM130 antibodies followed by appropriate secondary antibodies. Cells were visualized by fluorescence microscopy.

Statistical Analysis

Data are expressed as mean±SEM. Student's t tests were used to determine significant differences. $p<0.05$ was considered significant.

Reagents

Dulbecco's Modified Eagle's Medium (DMEM), DMEM/F12, fetal bovine serum (FBS), and penicillin streptomycin (PS) were from Gibco, mevalonolactone (M4667), oleic acid-albumin (O3008), crystal violet (C3886), cholesterol (C3045), mevastatin (M2537), tunicamycin (T7765), FLAG antibody (F4725), and lipoprotein-deficient serum (LPDS; S5394) were from Sigma-Aldrich; Lipofectamine 2000 was from Invitrogen; FuGENE HD transfection reagent and Dual-Glo Luciferase Assay Kit were from Promega; SuperScript VILO cDNA synthesis kit was from Thermo Fisher Scientific; S1P antibody (1280) was from Triple Point Biologics Inc.; KDEL antibody (SPA-827) was from Assay Designs, GM130 antibody (610823) was from BD Transduction Laboratories, and secondary IF antibodies were from Life Technologies. The SRD-12B cell line was obtained from the University of Texas-Southwestern Medical Center and Johns Hopkins School of Medicine.

DNA Constructs

The wild-type S1P construct encoded human S1P cDNA with a C-terminal Myc-DDK tag was generated by OriGene (RC212265, Rockville, Md.). S1P Pro1003Ser mutant construct encoding the c.3007 C>T missense mutation identified in the patient was generated by site-directed mutagenesis of the wild-type human S1P OriGene construct via QuikChange II Site-Directed Mutagenesis Kit (Agilent Technologies). Fatty acid synthase (FAS) promoter luciferase plasmid (FAS-Luc) encoding the fatty acid synthetase promoter upstream of luciferase obtained from Addgene. Constructs were verified via sequencing using appropriate primers.

Western Blotting

Whole-cell lysates were prepared using homogenization buffer (25 mM HEPES, 150 mM NaCl, 5 mM EDTA, 1% Triton X-100, pH 8.0) supplemented with 1 mM activated $Na_3VO_4$, 1 mM phenylmethanesulfonyl fluoride, 5 mM sodium fluoride, and 1× Complete protease inhibitor cocktail (Roche). Protein concentrations were determined by BCA assay (Pierce Biotechnology). Proteins were resolved by SDS-PAGE and S1P and tubulin were detected using appropriate antibodies. Blots were visualized using the LI-COR Odyssey imaging system.

RNA Extraction and Quantitative PCR:

RNA was extracted using RNA-Bee (Tel-Test, Inc.) as per manufacturer's instructions. cDNA was synthesized using the SuperScript VILO cDNA synthesis kit and gene expression quantified by real-time PCR using SYBR green reaction mix and appropriate primers. Human qPCR primers used:

```
MBTPS1
FWD
                                        (SEQ ID NO: 1)
5'-AGTTGGGAGTAAACAGCCCC-3',

REV
                                        (SEQ ID NO: 2)
5'-TCAATCAACCACTGTGAGCC-3';

farnesyl diphosphate (FDPS)
FWD
                                        (SEQ ID NO: 3)
5'-TCCATGATGTCATCTGCCAC-3', REV
                                        (SEQ ID NO: 4)
5'-AGCCAAGGAAACAGGATGC-3';
```

-continued

HMG CoA reductase (HMGCR)
FWD
(SEQ ID NO: 5)
5'-GATGGGAGGCCACAAAGAG-3',

REV
(SEQ ID NO: 6)
5'-TTCGGTGGCCTCTAGTGAGA-3';

squalene synthase (SQS)
FWD
(SEQ ID NO; 7)
5'-TCGGCAATCACTGTTTGGTA-3',

REV
(SEQ ID NO: 8)
5'-GGTTCATGGAGAGCAAGGAG-3';

acetyl coA carboxylase (ACACA)
FWD
(SEQ ID NO: 9)
5'-AGTGGGTCACCCCATTGTT-3',

REV
(SEQ ID NO: 10)
5'-TTCTAACAGGAGCTGGAGCC-3';

CHOP
FWD
(SEQ ID NO: 11)
5'-GGAGAACCAGGAAACGGAAAC-3',

REV
(SEQ ID NO: 12)
5'-TCTCCTTCATGCGCTGCTTT-3',

Grp78
FWD
(SEQ ID NO: 13)
5'-CATCACGCCGTCCTATGTCG-3',

REV
(SEQ ID NO: 14)
5'-GTCAAAGACCGTGTTCTCG-3', s-XBP1
FWD
(SEQ ID NO: 15)
5'-GGTCTGCTGAGTCCGCAGCAGG-3',

REV
(SEQ ID NO: 16)
5'-GGGCTTGGTATATATGTGG-3',

18s
FWD
(SEQ ID NO: 17)
5'-GAGGATGAGGTGGAACGTGT-3',

REV
(SEQ ID NO: 18)
5'-GGACCTGGCTGTATTTTCCA-3'.

Histology and Electron Microscopy

Cryostat sections of rapidly frozen muscle were processed as previously described. For ultrastructural analysis, a portion of the muscle biopsy was fixed by immersion in 3% glutaraldehyde in Karnovsky's buffer, pH 7.4, overnight at 4° C. Tissue samples were postfixed in Karynovsky's wash buffer, treated with 2% OsO$_4$, dehydrated in graded concentrations of ethanol, and embedded in EMbed-812 (Electron Microscopy Sciences, Hatfield, Pa.) with propylene oxide as an intermediary solvent. One-micron-thick plastic sections were examined by light microscopy after staining with toluidine blue. Ultrathin sections of muscle biopsies were cut onto mesh grids or Formvar-coated slot grids. Tissues were subsequently stained with uranyl acetate and lead citrate and examined with a JEOL 1200 electron microscope with an ABT digital camera.

Results

The proband presented to the neuromuscular clinic for evaluation of recurrent episodes of hyperCKemia with muscle fatigue, swelling, and myoedema. During her first reported episode, she presented with elevated levels of creatine kinase (8,517 U/L), aspartate aminotransferase (212 U/L), and alanine aminotransferase (145 U/L), despite not exercising for over a week prior to the incident. Her interictal serum creatine kinase levels were normal. Subsequent episodes of hyperCKemia developed within hours to days of moderate exercise. After the first episode she developed persistent muscle fatigue that was consistently exacerbated by heavy activity and exercise, but no objective motor deficits were evident on exam. Prior to her first episode of hyperCKemia, the patient had been highly athletic in high school and college, having competed in track and volleyball. As an infant, the patient had normal motor development and was born at full term. She sustained a broken kneecap and hip from a volleyball injury at age 20 but had no major musculoskeletal injuries or impairments. Additional clinical complications included small fiber and autonomic/enteric neuropathy complicated by chronic constipation, gastroparesis, gastrointestinal hypomotility and chronic nausea and vomiting, unexplained fevers with leukocytosis, ocular migraines, pelvic inflammatory disease, and polycystic ovary syndrome based on the Rotterdam criteria (Rotterdam ESHRE/ASRM-Sponsored PCOS Consensus Workshop Group, 2004).

Muscle histology revealed normal skeletal muscle structure, lipid content, fiber type distribution, and mitochondrial respiratory chain function (see e.g., FIG. 11A-FIG. 11D). Electron microscopy showed the patient's skeletal muscle had subtle disorganization of ultrastructure consisting of subsarcolemmal collections of mitochondria with scattered fat globules (see e.g., FIG. 11E) and mildly abnormal size and shape (see e.g., FIG. 11F); however, mitochondrial enzymatic activities were normal.

Figures 8A, 8B:
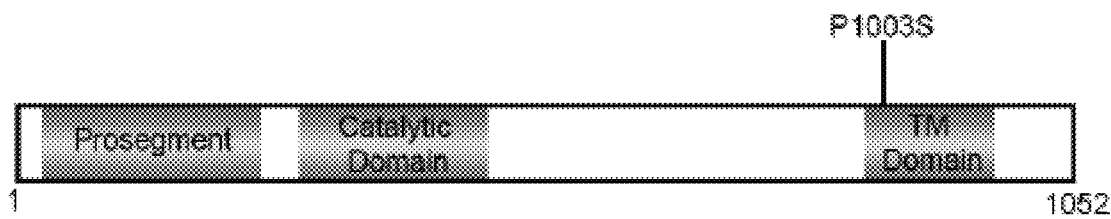
FIG. 8A-FIG. 8F is a series of schematics, graphs, and images showing genetic and functional analysis of S1P Pro1003Ser.

Whole exome and mitochondrial DNA sequencing of the proband and her parents revealed a heterozygous de novo missense mutation in exon 23 of the MBTPS1 (NM_003791.3 c.3007C>T) gene that corresponded to a single amino acid substitution in the transmembrane domain of S1P (NP_003782.1 p.Pro1003Ser) (see e.g., FIG. 8A). The gain of function mutation or the missense mutation in the transmembrane domain of S1P is Pro1003Ser mutation corresponding to SEQ ID NO: 20 in the transmembrane domain, wherein the mutated transmembrane domain of the S1P can comprise SEQ ID NO: 19, RYNQEVGQTISVFAFLGAMV.

Figure 8C:
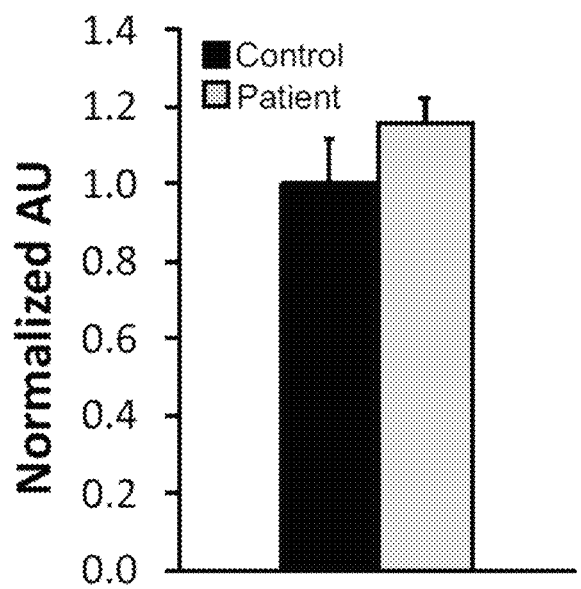
Figure 8D:
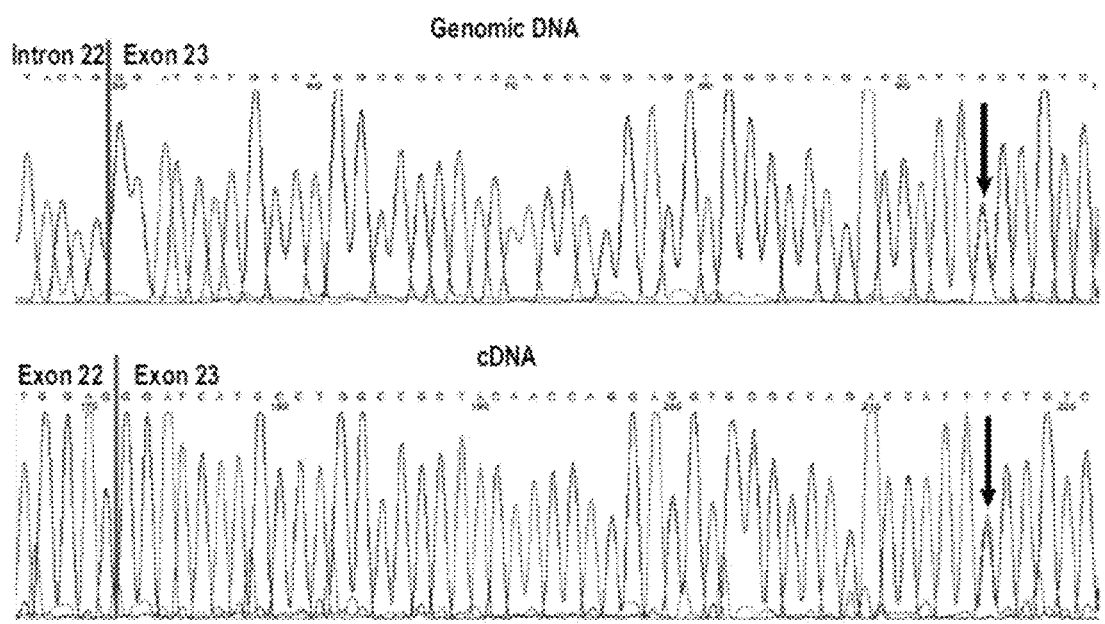

Proline 1003 is highly conserved across both v species (see e.g., FIG. 8B). The MBTPS1 was not identified in the ~6,500 individuals of European and African American ancestry in the NHLBI Exome Sequencing Project. This variant was not found among healthy controls based on ExAc and GnomAD; however, a mutation in the same codon (p.Pro1003His) was found in 1/108,864 European alleles by GnomAD. Substitution of a hydrophobic proline with a polar serine at residue 1003 within the transmembrane domain of S1P was predicted to be deleterious by Poly-Phen-2 (HDIV score 0.993; probably damaging), Align GVGD (score Class 65; most likely to interfere with function), and MutationTaster (p=0.999; disease causing), but not by SIFT (score 0.19; tolerated) (Adzhubei et al., 2010; Kumar, Henikoff, & Ng, 2009; Mathe et al., 2006; Schwarz, Cooper, Schuelke, & Seelow, 2014; Tavtigian et al., 2006). MBTPS1 transcript levels in proband-derived skin fibroblasts were similar to levels measured in control fibroblasts isolated from an individual without an S1P mutation (see e.g., FIG. 8C). Comparison of the Sanger sequencing trace files of the patient's genomic and cDNA-derived PCR products at the MBTPS1 c.3007C>T locus showed approximately equal expression of the wild-type and mutant transcripts (see e.g., FIG. 8D). Deep next generation sequencing of the patient cDNA-derived PCR products confirmed this observation, with 7216× coverage and approximately equal allele balance (3,452 wild-type alleles [47.8%] and 3,764 mutant alleles [52.2%]).

While disruption of S1P in mice decreases total plasma triglyceride and cholesterol levels (Yang et al., 2001), the patient's total plasma triglyceride and cholesterol levels were normal (TABLE 1) and her BMI was 20.7 kg/m$^2$.

TABLE 1

| S1P Pro1003Ser patient plasma lipid and cholesterol profile. | |
| --- | --- |
| Cholesterol (mg/dL) | 156 |
| HDL cholesterol (mg/dL) | 80 |
| LDL cholesterol (mg/dL) | 66 |
| Triglyceride (mg/dL) | 51 |

Figure 8E:
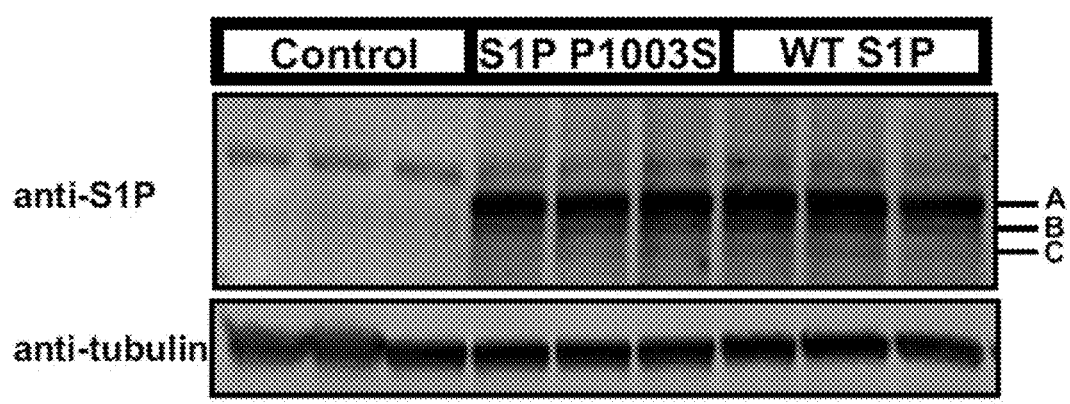

S1P must undergo multiple autocatalytic processing events in the ER before it can localize to the Golgi as an active mature protease (designated as C: 96 kDa estimated) (Espenshade et al., 1999; Ramos da Palma, Cendron, Seidah, Pasquato, & Kunz, 2015; Sakai et al., 1998). The ER-resident S1P precursors exist as a proprotein (designated as A: 115 kDa estimated) and an intermediate cleaved protein (designated as B: 102 kDa estimated) (Espenshade et al., 1999; Ramos da Palma et al., 2015). To examine whether the variant MBTPS1 allele produced these three S1P forms, a Chinese hamster ovary cell line that lacks S1P, SRD-12B, (Rawson et al., 1998) was transfected with plasmids encoding either human wild-type (WT) S1P or S1P Pro1003Ser with a C-terminal FLAG tag and visualized proteins via Western blot analysis. S1P Pro1003Ser-transfected cells expressed all three forms of S1P as did WT S1P-transfected cells (see e.g., FIG. 8E).

Figure 8F:
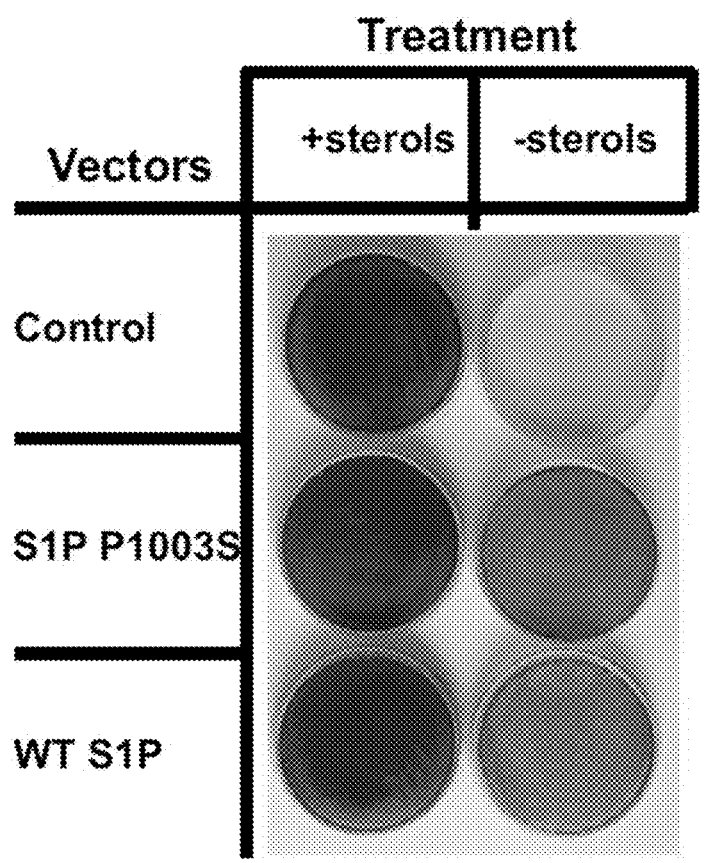

Because S1P is required for SREBP-dependent lipid and cholesterol biosynthesis, SRD-12B cells, which lack S1P, are lipid and cholesterol auxotrophs and must be supplemented with lipids and cholesterol to survive (Rawson et al., 1998). To test the functionality of S1P Pro1003Ser, a cell complementation assay was performed with SRD-12B cells transfected with human S1P Pro1003Ser or WT S1P and grew cells in the absence of lipids and cholesterol. While mock transfected SRD-12B cells failed to grow under these conditions, as reported previously (Rawson et al., 1998), SRD-12B cells that expressed S1P Pro1003Ser grew in the absence of supplemented lipids and cholesterol similar to WT S1P-expressing cells (see e.g., FIG. 8F).

Figure 10A:
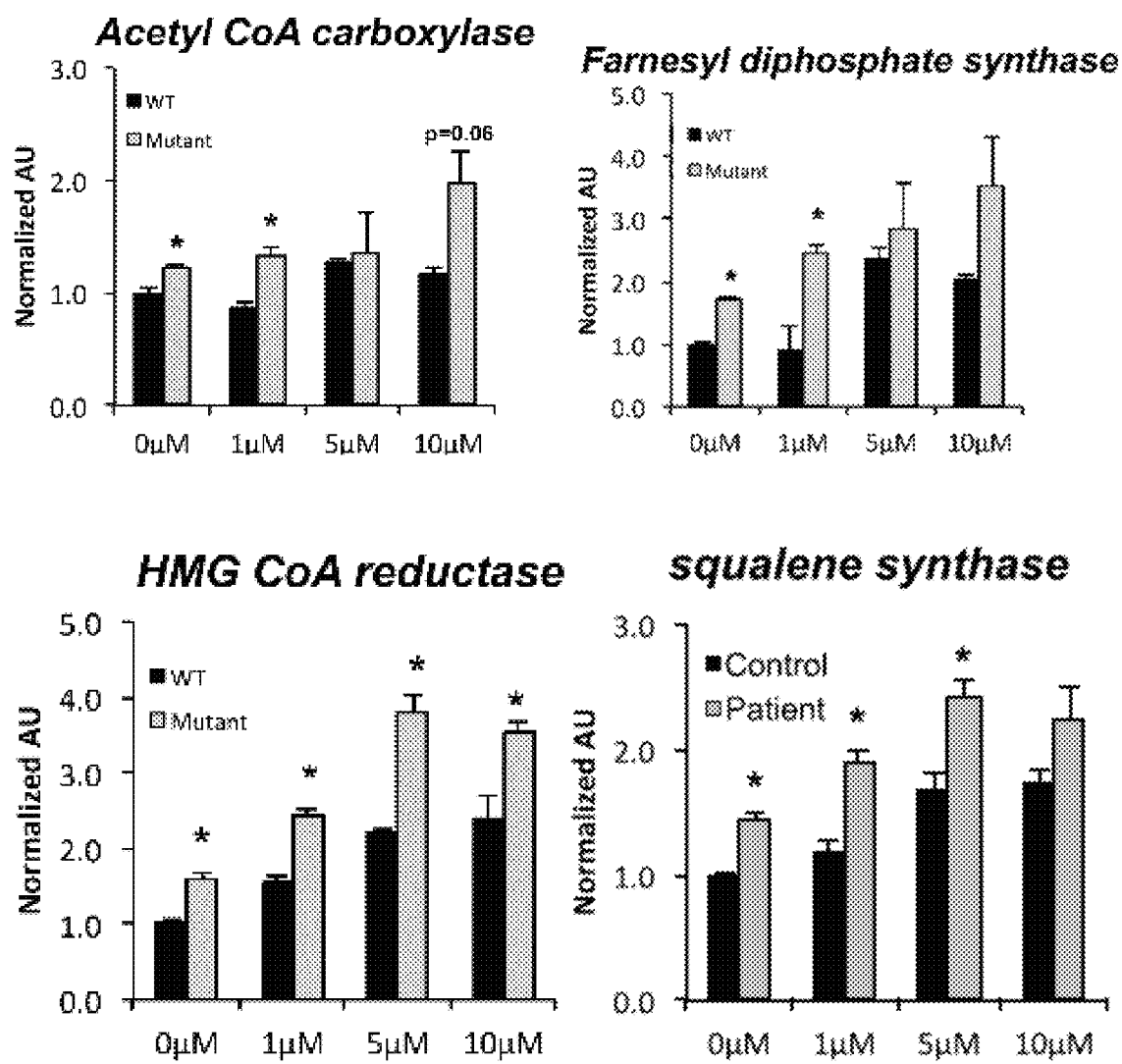
FIG. 10A-FIG. 10D is a series of bar graphs and images showing S1P Pro1003Ser has enhanced activity and accumulates in the Golgi. mRNA expression levels in cultured control- and patient-derived skin fibroblasts of SREBP1 and 2 target genes after 4 hr of treatment with the indicated concentrations of mevastatin are shown in FIG. 10A and UPR and ATF6 target genes following treatment with 1 µg/ml of tunicamycin for 4, 8, and 12 hr are shown in FIG. 10B.
Figure 10B:
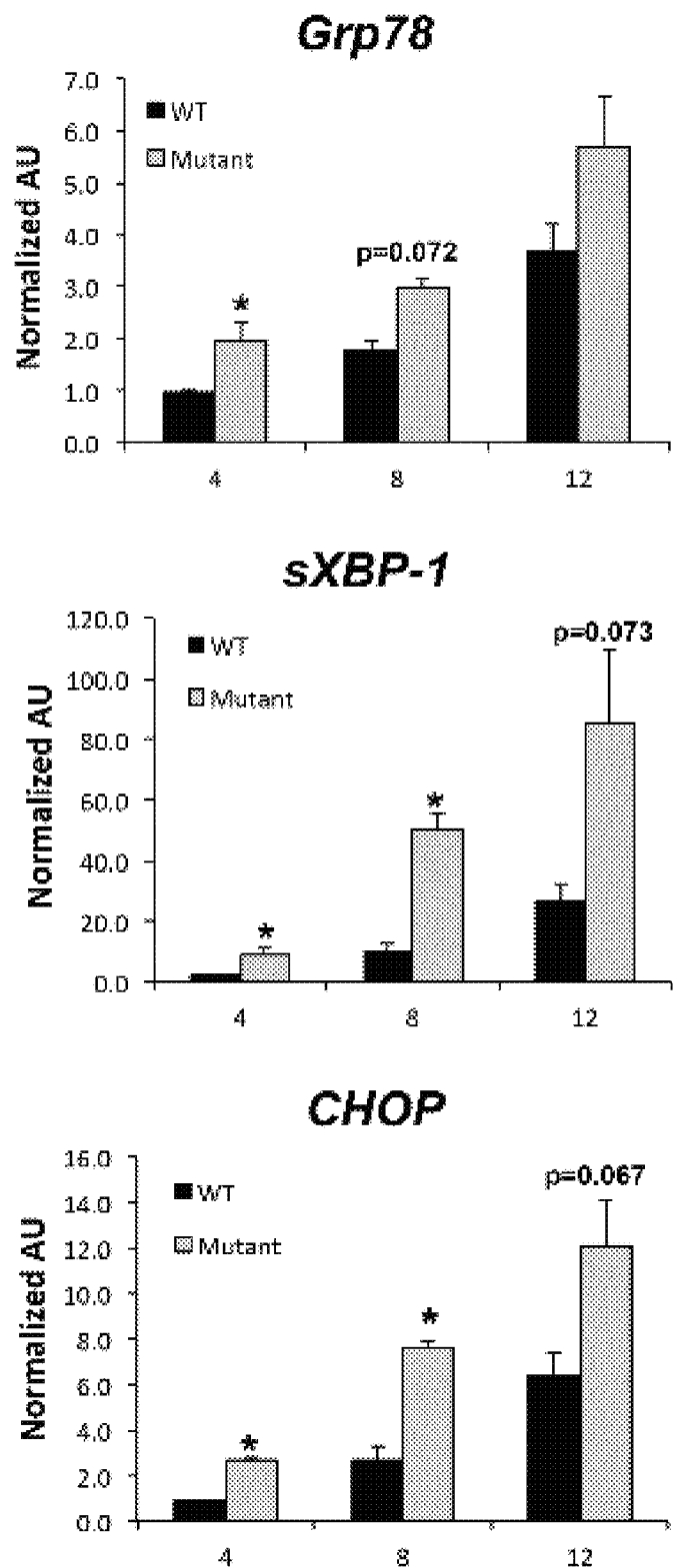
Figure 10C:
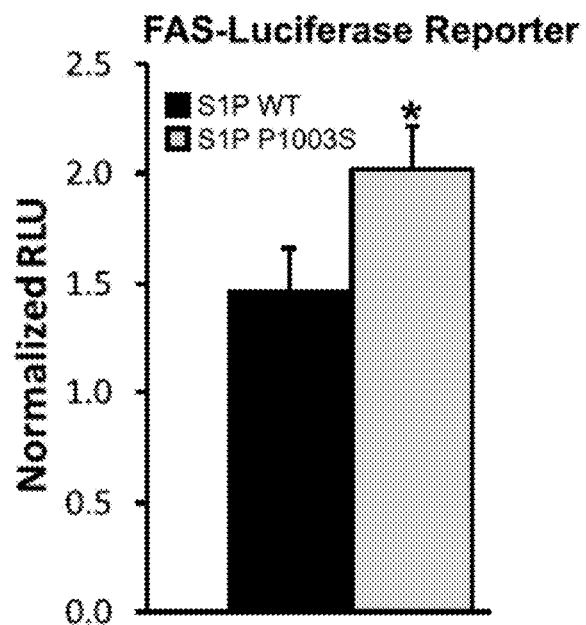
Figure 10D:
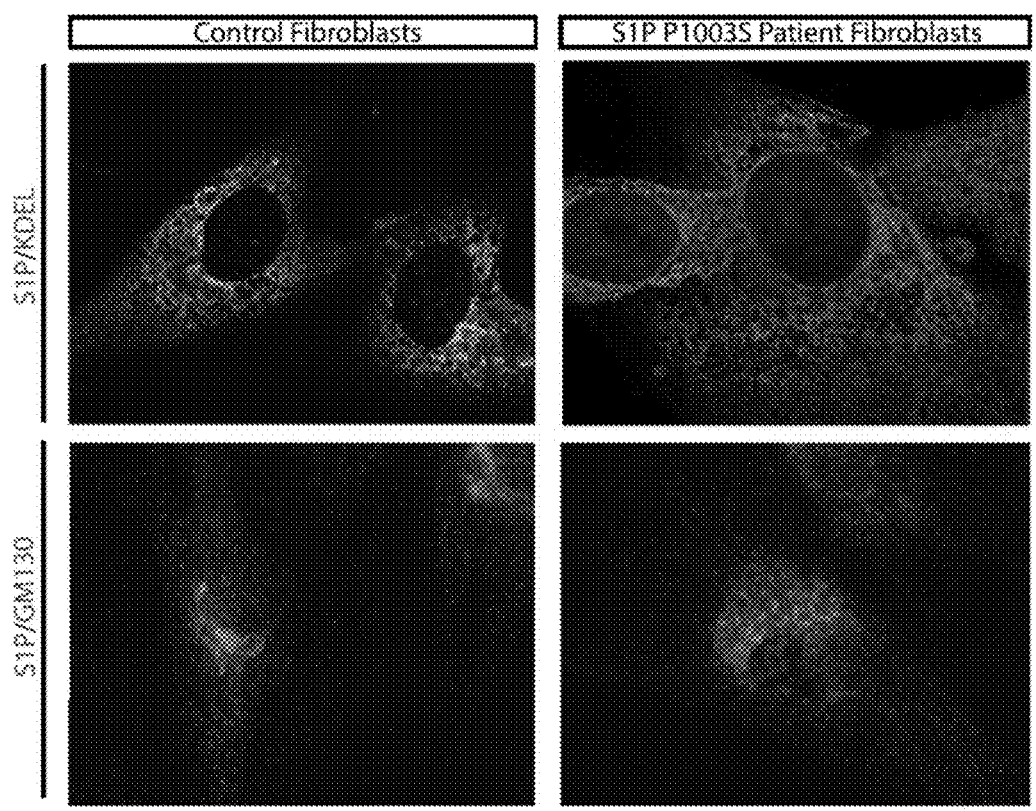
Figures 11A, 11B, 11C, 11D, 11E, 11F:
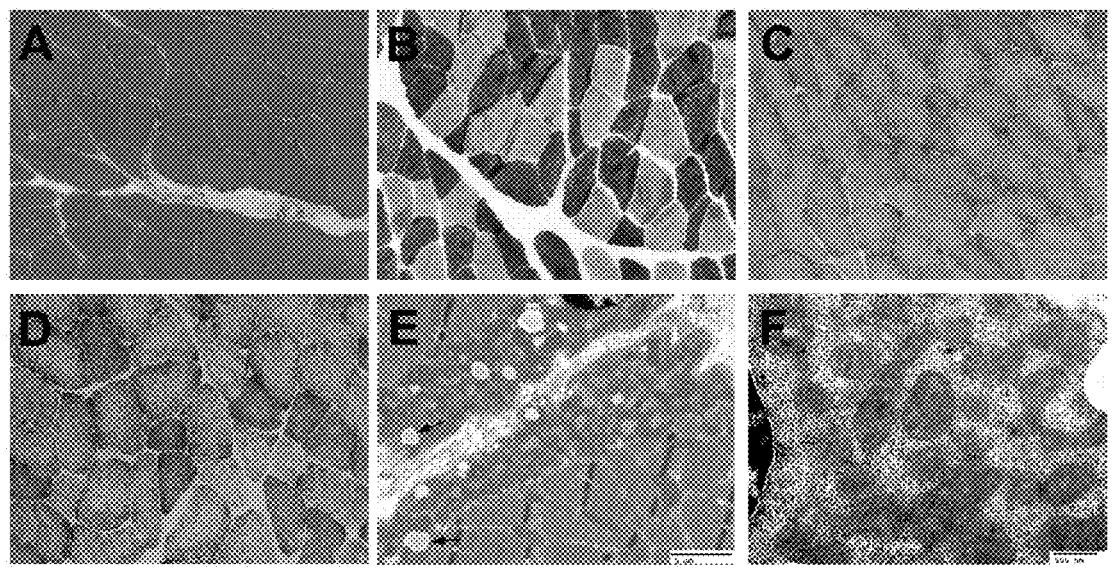
FIG. 11A-FIG. 11F is a series of images showing histological and electron microscopy analysis of patient skeletal muscle. Patient quadricep muscle was stained as indicated and representative images are shown.
Figure 12:
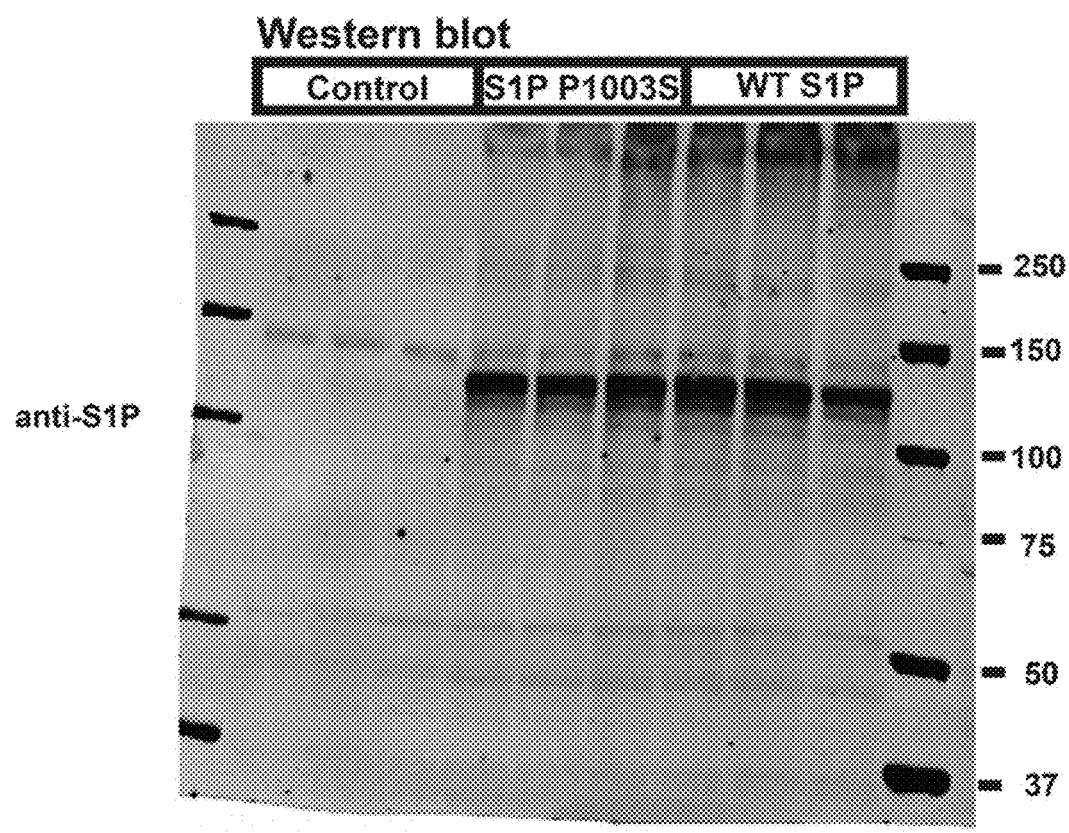
FIG. 12 is an image of an entire anti-S1P Western blot of SRD-12B cells expressing S1P P1003S or WT S1P. Molecular weight markers and corresponding kilodalton (kDa) values are indicated.
Figure 13:
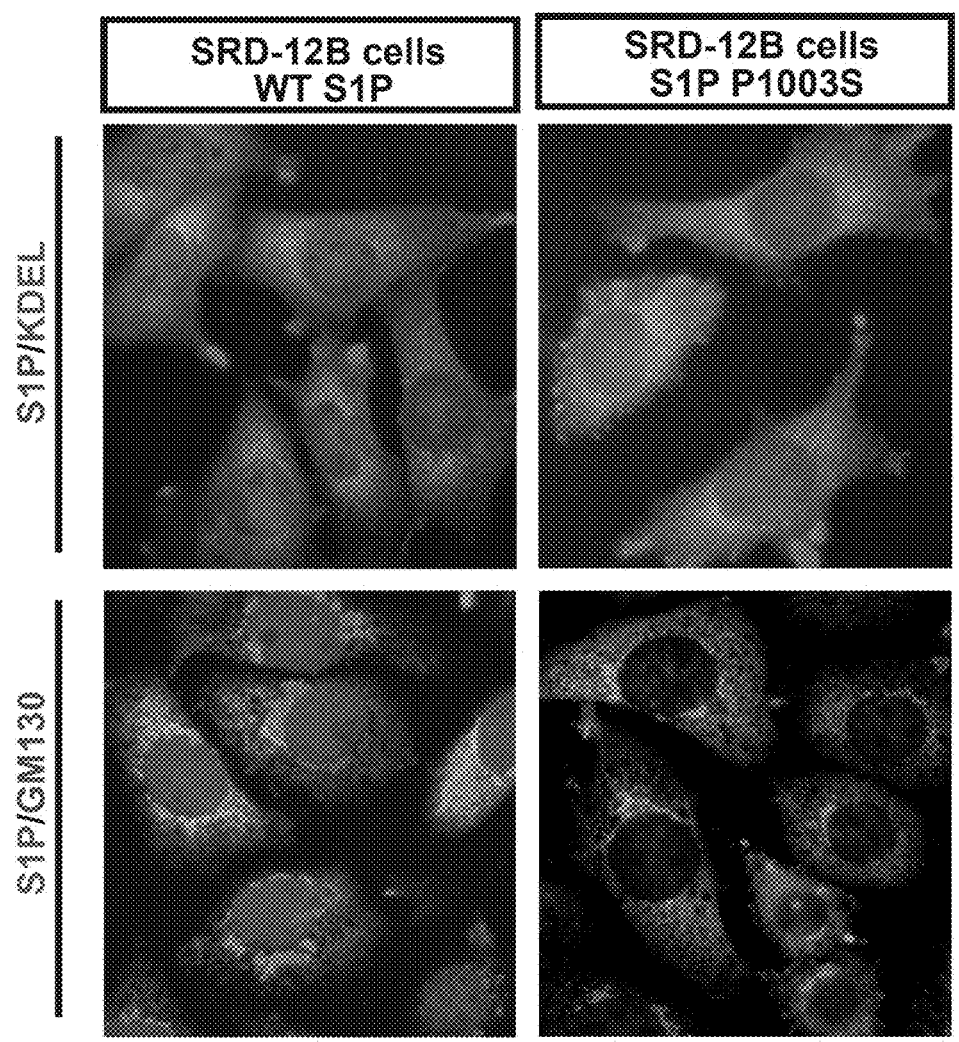
FIG. 13 is an image showing S1P localization in transfected SRD-12B cells. Immunofluorescence of SRD-12B cells transiently transfected with a construct encoding hen egg lysozyme C-terminally tagged with GFP and the ER retention signal KDEL and either FLAG-tagged WT S1P or S1P Pro1003Ser. Representative images are shown. Antibodies against FLAG and GM130 (Golgi marker) were used to visualize protein localization.

To further examine the functionality of S1P Pro1003Ser, the mutant's ability to activate its substrate pathways, SREBP and ATF6, was tested using S1P Pro1003Ser patient-derived fibroblasts and control fibroblasts from an individual without an S1P mutation. Treatment of sterol-depleted cells with the HMG-CoA reductase inhibitor mevastatin (compactin) promotes transcription of SREBP1a and 2 target genes (Brown, Faust, Goldstein, Kaneko, & Endo, 1978; Shimomura, Shimano, Horton, Goldstein, & Brown, 1997). Whether S1P Pro1003Ser patient-derived fibroblasts respond to mevastatin treatment was examined, here. S1P Pro1003Ser fibroblasts showed a dosage-dependent increase in the expression of SREBP1 and 2 target genes that was higher than the expression levels of treated control fibroblasts (see e.g., FIG. 10A). Even in the absence of mevastatin, expression levels of SREBP1 and 2 target genes were elevated in S1P Pro1003Ser fibroblasts compared to control fibroblasts (see e.g., FIG. 10A). Tested next was whether S1P Pro1003Ser could activate ATF6, a transcription factor required to restore ER homeostasis during ER stress, by treating fibroblasts with tunicamycin to induce ER stress. S1P Pro1003Ser patient fibroblasts treated with tunicamycin had higher expression levels of spliced XBP-1 and the ATF6 target genes Grp78 and CHOP than control fibroblasts (see e.g., FIG. 10B). To determine whether S1P Pro1003Ser could directly activate SREBPs, a luciferase reporter assay was performed using an SREBP1-response fatty acid synthase luciferase promoter construct. SRD-12B cells expressing S1P Pro1003Ser exhibited higher levels of SREBP1-dependent promoter activity than cells expressing WT S1P (see e.g., FIG. 10C). The intracellular localization of mature S1P and its substrates to the Golgi is an important regulatory mechanism that governs S1P function (DeBose-Boyd et al., 1999; Marschner et al., 2011; Nohturfft, DeBose-Boyd, Scheek, Goldstein, & Brown, 1999; Raggo et al., 2002; Sakai et al., 1998; Shen, Chen, Hendershot, & Prywes, 2002; Stirling & O'hare, 2006; Ye et al., 2000). To begin to understand the mechanism behind the enhanced activity of S1P Pro1003Ser, it was investigated whether S1P Pro1003Ser localization was altered in the patient's fibroblasts. Control and patient fibroblasts were transfected with either FLAG-tagged human WT S1P or S1P Pro1003Ser, respectively, and double-labeled with anti-FLAG and antibodies against KDEL-bearing proteins (ER marker) and GM130 (Golgi marker) (see e.g., FIG. 10D). Similar to WT S1P, S1P Pro1003Ser localized to both the ER and the Golgi. This result was also observed when performed in SRD-12B cells transfected with WT S1P and S1P Pro1003Ser (see e.g., FIG. 13).

Discussion

In conclusion, described here is a patient with a de novo heterozygous variant in the gene MBTPS1 that produces a missense mutation in the transmembrane domain of S1P. Deep next generation sequencing showed that the mutant MBTPS1 transcript is expressed at levels similar to the wild-type transcript in patient-derived skin fibroblasts. The patient presented with a complex phenotype that included episodic hyperCKemia, focal myoedema, ocular migraines, and polycystic ovary syndrome. To date, associations between thes ations and S1P have not been described.

The presently described functional analysis showed the MBTPS1 variant produces a stable S1P Pro1003Ser protease that is able to complement lipid and cholesterol biosynthetic capacities in cells that lack S1P and is abundant in both the ER and the Golgi. S1P Pro1003Ser exhibited enhanced activation of SREBP and UPR pathways compared to WT S1P, suggesting this mutant protein has an altered function, possibly a gain-of-function.

Reports have shown S1P can exist as multiple shed ectodomain species (Elagoz et al., 2002; Kim et al., 2018). While S1P Pro1003Ser produced the unprocessed precursor, an intermediate cleaved product, and the mature protease, shed ectodomain species were unable to be detected. This may be due to differences in culture conditions—indeed it has been shown that production of some shed S1P species requires specific conditions (e.g., increased Caspase-2 expression, mouse models of nonalcoholic steatohepatitis) (Kim et al., 2018) and/or due to differences in methodology (Elagoz et al. visualized shed S1P most abundantly in culture media via radiolabeling coupled with immunoprecipitation, while here standard Western blots of whole-cell lysates was performed).

S1P functions in concert with Site-2 Protease (S2P) to activate substrates (Espenshade & Hughes, 2007). Loss-of-function S2P mutations are well documented as contributors to human disease including skeletal dysplasia (Aten et al., 2010; Bornholdt et al., 2013; Haghighi et al., 2013; Lindert et al., 2016; Naiki et al., 2012; Nakayama et al., 2011; Oeffner et al., 2009; Zhang et al., 2016). A recent study reported a case of human skeletal dysplasia in a pediatric patient with an S1P deficiency, resulting in disrupted ER stress, but retained lipid homeostasis (Kondo et al., 2018). Based on the thorough clinical analysis, such S2P- and S1P-associated syndromes were not present in the proband, most likely due to the loss-of-function nature of those previously identified mutations.

The S1P Pro1003Ser patient phenotype is complex and includes conditions that effect several organs including skeletal muscle and the ovary. These observations suggest that S1P may play a critical role in the functions of these organs in ways that are not yet understood, either via well-known S1P substrates or yet to be identified substrates. These observations underscore the importance of S1P in human physiology and shed light on a potential role for S1 verse array of human disorders and organ systems.

Example 3: S1P Inhibitor Increased Exercise Endurance

The following example describes an S1P inhibitor increasing or improving exercise endurance or tolerance in mice.

Wild-type mice were treated with PF-429242 or vehicle via intraperitoneal injection, and subjected to an acute exercise test to exhaustion (N=3).

Figure 14:
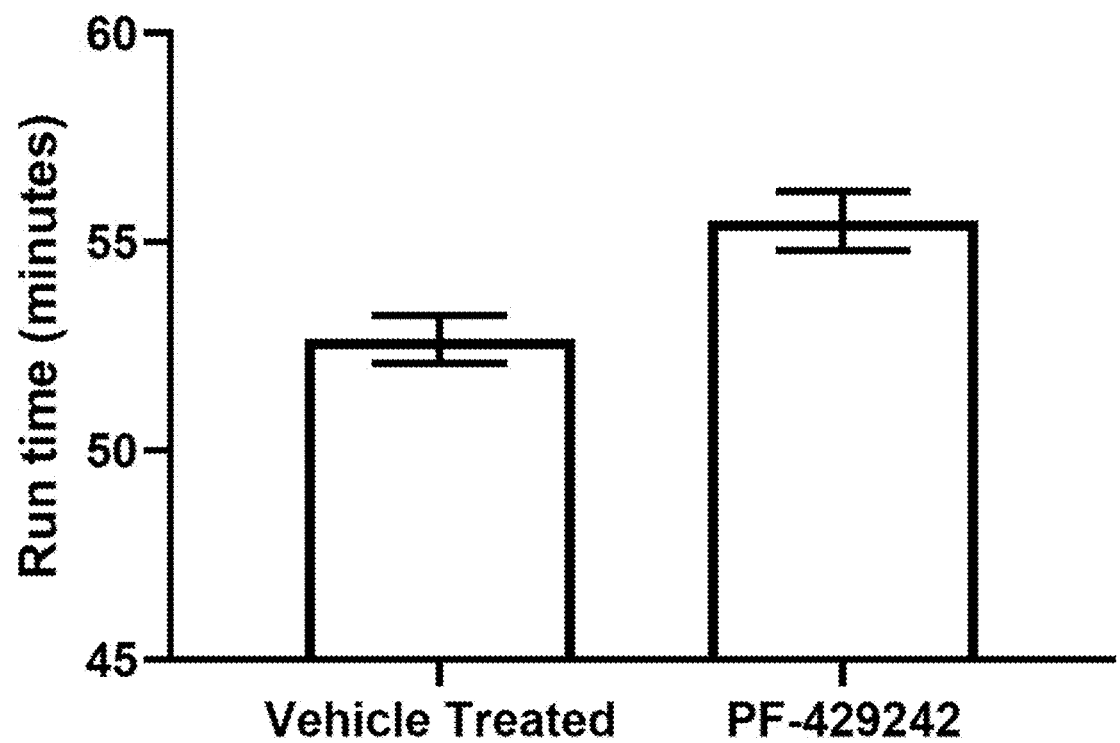
FIG. 14 is a bar graph depicting wild-type mice treated with PF-429242 or vehicle via intraperitoneal injection, and subjected to an acute exercise test to exhaustion (N=3).

The wild-type mice display enhanced exercise tolerance compared to WT littermates (see e.g., FIG. 14).

Experiments for optimizing drug concentrations and time of treatment to ensure complete S1P inhibition in skeletal muscle will be performed using standard techniques.

What is claimed is:

1. A method of improving exercise tolerance or enhancing exercise performance in a subject comprising:
   administering a pharmaceutical composition comprising a S1P inhibiting agent in an amount effective to reduce or deplete S1P levels or reduce or deplete S1P activity in the subject and improve exercise tolerance or enhance exercise performance compared to the subject prior to being administered the pharmaceutical composition, wherein the subject has a mutation in a gene encoding S1P (MBTPS1) that results in an increase in S1P protein that is expressed or an increase in activity of S1P target pathways compared to a subject having wild type MBTPS1.

2. The method of claim 1, wherein the mutation is a replacement of proline with serine in a transmembrane domain of S1P at a position corresponding to position 1003 of SEQ ID NO: 20, and the transmembrane domain of the mutant S1P comprises instant SEQ ID NO: 19.

3. A method of treating a disease, disorder, or condition associated with reduced exercise tolerance or endurance in a subject comprising administering a pharmaceutical composition comprising a S1P inhibiting agent in an amount effective to reduce or deplete S1P levels or reduce or deplete S1P activity in the subject and improve exercise tolerance or enhance exercise performance compared to the subject prior to being administered the pharmaceutical composition, wherein the subject has a mutation in a gene encoding S1P (MBTPS1) that results in an increase in S1P protein that is expressed or an increase in activity of S1P target pathways compared to a normal subject having wild type MBTPS1.

4. The method of claim 3, wherein, after being administered the pharmaceutical composition, the subject exhibits:

increased expression of genes encoding enzymes involved in fatty acid metabolism;
higher capacity for fatty acid oxidation;
enhanced mitochondrial metabolism;
reduced respiratory exchange ratio (RER) value;
increased long-chain fatty acid (LCFA) muscle uptake;
elevated markers of fatty acid oxidation; or
decreased serum triglyceride (TAG) levels;
optionally, in response to exercise stimulus,
compared to the subject prior to being administered the pharmaceutical composition.

5. The method of claim 3, wherein the subject has a gain of function mutation or a missense mutation in a S1P transmembrane domain, wherein the gain of function mutation or the missense mutation is a replacement of proline with serine in a transmembrane domain of S1P at a position corresponding to position 1003 of SEQ ID NO: 20, and the transmembrane domain of the mutant S1P comprises instant SEQ ID NO: 19.

6. The method of claim 3, wherein the subject has or is suspected of having obesity, type 2 diabetes (T2DM), heart failure (HF), cardiovascular disease (CVD), insulin resistance, hypertension, hyperCKemia, myoedema, rhabdomyolysis, idiopathic chronic muscle fatigue, cardiac abnormalities, or dysfunctional muscle or heart.

7. The method of claim 3, wherein the subject has muscle fatigue, swelling, or myoedema during or after moderate physical activity compared to a subject having wild type MBTPS1.

8. The method of claim 3, wherein the subject is a mammal selected from a human, horse, or dog.

9. The method of claim 3, wherein the S1P inhibiting agent is a small molecule inhibitor of S1P or a genetic inhibitor selected from an shRNA, an siRNA, and an antisense oligonucleotide (ASO), wherein the genetic inhibitor targets S1P mRNA and reduces, eliminates, or inhibits expression or activity of S1P.

10. The method of claim 3, wherein the S1P inhibiting agent is PF-429242:

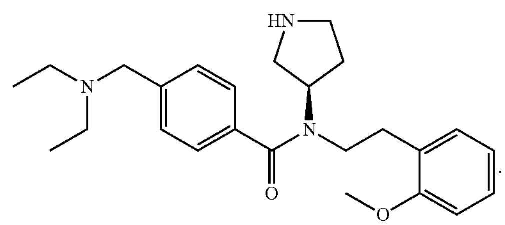

4-[(Diethylamino)methyl]-N-[2-(2-methoxyphenyl)ethyl]-N-(3R)-3-pyrrolidinyl-benzamide 11. The method of claim 1, wherein the increase in activity of S1P target pathways is selected from enhanced activation of SREBP, enhanced activation of UPR, or enhanced activation of ATF6.

12. The method of claim 3, wherein the increase in activity of S1 P target pathways is selected from enhanced activation of SREBP, enhanced activation of UPR, or enhanced activation of ATF6.

* * * * *

```
                           SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
agttgggagt aaacagcccc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
tcaatcaacc actgtgagcc                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
tccatgatgt catctgccac                                              20

<210> SEQ ID NO 4
<211> LENGTH: 19
<212> TYPE: DNA
<213> ORGANISM: Artificial Sequence
<220> FEATURE:
<223> OTHER INFORMATION: Synthetic primer

<400> SEQUENCE: 4
agccaaggaa acaggatgc                                               19

<210> SEQ ID NO 5
```

<211> LENGTH: 19
<212> TYPE: DNA
<213> ORGANISM: Artificial Sequence
<220> FEATURE:
<223> OTHER INFORMATION: Synthetic primer

<400> SEQUENCE: 5
gatgggaggc cacaaagag                                               19

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
ttcggtggcc tctagtgaga                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
tcggcaatca ctgtttggta                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ggttcatgga gagcaaggag                                              20

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
agtgggtcac cccattgtt                                               19

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
ttctaacagg agctggagcc                                              20

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
ggagaaccag gaaacggaaa c                                              21

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
tctccttcat gcgctgcttt                                                20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
catcacgccg tcctatgtcg                                                20

<210> SEQ ID NO 14
<211> LENGTH: 19
<212> TYPE: DNA
<213> ORGANISM: Artificial Sequence
<220> FEATURE:
<223> OTHER INFORMATION: Synthetic primer

<400> SEQUENCE: 14
gtcaaagacc gtgttctcg                                                 19

<210> SEQ ID NO 15
<211> LENGTH: 22
<212> TYPE: DNA
<213> ORGANISM: Artificial Sequence
<220> FEATURE:
<223> OTHER INFORMATION: Synthetic primer

<400> SEQUENCE: 15
ggtctgctga gtccgcagca gg                                             22

<210> SEQ ID NO 16
<211> LENGTH: 19
<212> TYPE: DNA
<213> ORGANISM: Artificial Sequence
<220> FEATURE:
<223> OTHER INFORMATION: Synthetic primer

<400> SEQUENCE: 16
gggcttggta tatatgtgg                                                 19

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
gaggatgagg tggaacgtgt                                                20

<210> SEQ ID NO 18
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 18
ggacctggct gtattttcca                                              20

<210> SEQ ID NO 19
<211> LENGTH: 20
<212> TYPE: PRT
<213> ORGANISM: Homo sapiens

<400> SEQUENCE: 19

Arg Tyr Asn Gln Glu Val Gln Gly Thr Ile Ser Val Phe Ala Phe Leu
1               5                   10                  15

Gly Ala Met Val
            20

<210> SEQ ID NO 20
<211> LENGTH: 1052
<212> TYPE: PRT
<213> ORGANISM: Homo sapiens

<400> SEQUENCE: 20

Met Lys Leu Val Asn Ile Trp Leu Leu Leu Val Val Leu Leu Cys
1               5                   10                  15

Gly Lys Lys His Leu Gly Asp Arg Leu Glu Lys Lys Ser Phe Glu Lys
                20                  25                  30

Ala Pro Cys Pro Gly Cys Ser His Leu Thr Leu Lys Val Glu Phe Ser
            35                  40                  45

Ser Thr Val Val Glu Tyr Glu Tyr Ile Val Ala Phe Asn Gly Tyr Phe
        50                  55                  60

Thr Ala Lys Ala Arg Asn Ser Phe Ile Ser Ser Ala Leu Lys Ser Ser
65                  70                  75                  80

Glu Val Asp Asn Trp Arg Ile Ile Pro Arg Asn Asn Pro Ser Ser Asp
                85                  90                  95

Tyr Pro Ser Asp Phe Glu Val Ile Gln Ile Lys Glu Lys Gln Lys Ala
            100                 105                 110

Gly Leu Leu Thr Leu Glu Asp His Pro Asn Ile Lys Arg Val Thr Pro
        115                 120                 125

Gln Arg Lys Val Phe Arg Ser Leu Lys Tyr Ala Glu Ser Asp Pro Thr
    130                 135                 140

Val Pro Cys Asn Glu Thr Arg Trp Ser Gln Lys Trp Gln Ser Ser Arg
145                 150                 155                 160

Pro Leu Arg Arg Ala Ser Leu Ser Leu Gly Ser Gly Phe Trp His Ala
                165                 170                 175

Thr Gly Arg His Ser Ser Arg Arg Leu Leu Arg Ala Ile Pro Arg Gln
            180                 185                 190

Val Ala Gln Thr Leu Gln Ala Asp Val Leu Trp Gln Met Gly Tyr Thr
        195                 200                 205

Gly Ala Asn Val Arg Val Ala Val Phe Asp Thr Gly Leu Ser Glu Lys
    210                 215                 220

His Pro His Phe Lys Asn Val Lys Glu Arg Thr Asn Trp Thr Asn Glu
225                 230                 235                 240

Arg Thr Leu Asp Asp Gly Leu Gly His Gly Thr Phe Val Ala Gly Val
                245                 250                 255

Ile Ala Ser Met Arg Glu Cys Gln Gly Phe Ala Pro Asp Ala Glu Leu
```

```
                    260                 265                 270
His Ile Phe Arg Val Phe Thr Asn Asn Gln Val Ser Tyr Thr Ser Trp
                275                 280                 285

Phe Leu Asp Ala Phe Asn Tyr Ala Ile Leu Lys Lys Ile Asp Val Leu
                290                 295                 300

Asn Leu Ser Ile Gly Gly Pro Asp Phe Met Asp His Pro Phe Val Asp
305                 310                 315                 320

Lys Val Trp Glu Leu Thr Ala Asn Asn Val Ile Met Val Ser Ala Ile
                325                 330                 335

Gly Asn Asp Gly Pro Leu Tyr Gly Thr Leu Asn Asn Pro Ala Asp Gln
                340                 345                 350

Met Asp Val Ile Gly Val Gly Gly Ile Asp Phe Glu Asp Asn Ile Ala
                355                 360                 365

Arg Phe Ser Ser Arg Gly Met Thr Thr Trp Glu Leu Pro Gly Gly Tyr
                370                 375                 380

Gly Arg Met Lys Pro Asp Ile Val Thr Tyr Gly Ala Gly Val Arg Gly
385                 390                 395                 400

Ser Gly Val Lys Gly Gly Cys Arg Ala Leu Ser Gly Thr Ser Val Ala
                405                 410                 415

Ser Pro Val Val Ala Gly Ala Val Thr Leu Leu Val Ser Thr Val Gln
                420                 425                 430

Lys Arg Glu Leu Val Asn Pro Ala Ser Met Lys Gln Ala Leu Ile Ala
                435                 440                 445

Ser Ala Arg Arg Leu Pro Gly Val Asn Met Phe Glu Gln Gly His Gly
                450                 455                 460

Lys Leu Asp Leu Leu Arg Ala Tyr Gln Ile Leu Asn Ser Tyr Lys Pro
465                 470                 475                 480

Gln Ala Ser Leu Ser Pro Ser Tyr Ile Asp Leu Thr Glu Cys Pro Tyr
                485                 490                 495

Met Trp Pro Tyr Cys Ser Gln Pro Ile Tyr Tyr Gly Gly Met Pro Thr
                500                 505                 510

Val Val Asn Val Thr Ile Leu Asn Gly Met Gly Val Thr Gly Arg Ile
                515                 520                 525

Val Asp Lys Pro Asp Trp Gln Pro Tyr Leu Pro Gln Asn Gly Asp Asn
                530                 535                 540

Ile Glu Val Ala Phe Ser Tyr Ser Ser Val Leu Trp Pro Trp Ser Gly
545                 550                 555                 560

Tyr Leu Ala Ile Ser Ile Ser Val Thr Lys Lys Ala Ala Ser Trp Glu
                565                 570                 575

Gly Ile Ala Gln Gly His Val Met Ile Thr Val Ala Ser Pro Ala Glu
                580                 585                 590

Thr Glu Ser Lys Asn Gly Ala Glu Gln Thr Ser Thr Val Lys Leu Pro
                595                 600                 605

Ile Lys Val Lys Ile Ile Pro Thr Pro Arg Ser Lys Arg Val Leu
                610                 615                 620

Trp Asp Gln Tyr His Asn Leu Arg Tyr Pro Gly Tyr Phe Pro Arg
625                 630                 635                 640

Asp Asn Leu Arg Met Lys Asn Asp Pro Leu Asp Trp Asn Gly Asp His
                645                 650                 655

Ile His Thr Asn Phe Arg Asp Met Tyr Gln His Leu Arg Ser Met Gly
                660                 665                 670

Tyr Phe Val Glu Val Leu Gly Ala Pro Phe Thr Cys Phe Asp Ala Ser
                675                 680                 685
```

```
Gln Tyr Gly Thr Leu Leu Met Val Asp Ser Glu Glu Tyr Phe Pro
690                 695                 700
Glu Glu Ile Ala Lys Leu Arg Arg Asp Val Asp Asn Gly Leu Ser Leu
705             710                 715                 720
Val Ile Phe Ser Asp Trp Tyr Asn Thr Ser Val Met Arg Lys Val Lys
                725                 730                 735
Phe Tyr Asp Glu Asn Thr Arg Gln Trp Trp Met Pro Asp Thr Gly Gly
            740                 745                 750
Ala Asn Ile Pro Ala Leu Asn Glu Leu Leu Ser Val Trp Asn Met Gly
            755                 760                 765
Phe Ser Asp Gly Leu Tyr Glu Gly Glu Phe Thr Leu Ala Asn His Asp
            770                 775                 780
Met Tyr Tyr Ala Ser Gly Cys Ser Ile Ala Lys Phe Pro Glu Asp Gly
785                 790                 795                 800
Val Val Ile Thr Gln Thr Phe Lys Asp Gln Gly Leu Glu Val Leu Lys
                805                 810                 815
Gln Glu Thr Ala Val Val Glu Asn Val Pro Ile Leu Gly Leu Tyr Gln
            820                 825                 830
Ile Pro Ala Glu Gly Gly Arg Ile Val Leu Tyr Gly Asp Ser Asn
            835                 840                 845
Cys Leu Asp Asp Ser His Arg Gln Lys Asp Cys Phe Trp Leu Leu Asp
850                 855                 860
Ala Leu Leu Gln Tyr Thr Ser Tyr Gly Val Thr Pro Pro Ser Leu Ser
865             870                 875                 880
His Ser Gly Asn Arg Gln Arg Pro Pro Ser Gly Ala Gly Ser Val Thr
                885                 890                 895
Pro Glu Arg Met Glu Gly Asn His Leu His Arg Tyr Ser Lys Val Leu
            900                 905                 910
Glu Ala His Leu Gly Asp Pro Lys Pro Arg Pro Leu Pro Ala Cys Pro
            915                 920                 925
Arg Leu Ser Trp Ala Lys Pro Gln Pro Leu Asn Glu Thr Ala Pro Ser
930                 935                 940
Asn Leu Trp Lys His Gln Lys Leu Leu Ser Ile Asp Leu Asp Lys Val
945                 950                 955                 960
Val Leu Pro Asn Phe Arg Ser Asn Arg Pro Gln Val Arg Pro Leu Ser
                965                 970                 975
Pro Gly Glu Ser Gly Ala Trp Asp Ile Pro Gly Gly Ile Met Pro Gly
            980                 985                 990
Arg Tyr Asn Gln Glu Val Gly Gln Thr Ile Pro Val Phe Ala Phe Leu
            995                 1000                1005
Gly Ala Met Val Val Leu Ala Phe Phe Val Val Gln Ile Asn Lys
    1010                1015                1020
Ala Lys Ser Arg Pro Lys Arg Arg Lys Pro Arg Val Lys Arg Pro
    1025                1030                1035
Gln Leu Met Gln Gln Val His Pro Pro Lys Thr Pro Ser Val
    1040                1045                1050
```